United States Patent [19]
Murnane et al.

[11] Patent Number: 5,395,767
[45] Date of Patent: Mar. 7, 1995

[54] GENE FOR ATAXIA-TELANGIECTASIA COMPLEMENTATION GROUP D (ATDC)

[75] Inventors: John P. Murnane, San Francisco; Robert B. Painter, Burlingame; Leon N. Kapp, San Rafael; Loh-Chung Yu, Redwood City, all of Calif.

[73] Assignee: Regents of the University of California, California, Calif.

[21] Appl. No.: 903,466

[22] Filed: Jun. 22, 1992

[51] Int. Cl.⁶ .................... C12N 15/00; C07H 21/04
[52] U.S. Cl. ................... 435/320.1; 435/69.1; 435/240.1; 536/23.1; 536/24.3
[58] Field of Search ............... 435/69.1, 240.2, 320.1, 435/6; 536/23.1, 24.3

[56] References Cited

PUBLICATIONS

Jacobs et al., 1985, Nature, vol. 313, pp. 806–810.
Foroud et al., *Am. J. Hum. Genet.*, 49: 1263–1279 (1991).
Kapp and Painter, *Int. J. Radiat. Biol.*, 56 (5): 667–675 (1989).
Lambert et al., *PNAS* (USA), 88: 5907–5911 (Jul. 1991).
McConville et al., *Nucleic Acids Research*, 18 (15): 4335–4343.

*Primary Examiner*—Garnette D. Draper
*Assistant Examiner*—Sally P. Teng
*Attorney, Agent, or Firm*—Leona L. Lauder

[57] ABSTRACT

Disclosed herein is a new gene, an AT gene for complementation group D, the ATDC gene and fragments thereof. Nucleic acid probes for said gene are provided as well as proteins encoded by said gene, cDNA therefrom, preferably a 3 kilobase (kb) cDNA, and recombinant nucleic acid molecules for expression of said proteins. Further disclosed are methods to detect mutations in said gene, preferably methods employing the polymerase chain reaction (PCR). Also disclosed are methods to detect AT genes from other AT complementation groups.

10 Claims, 23 Drawing Sheets

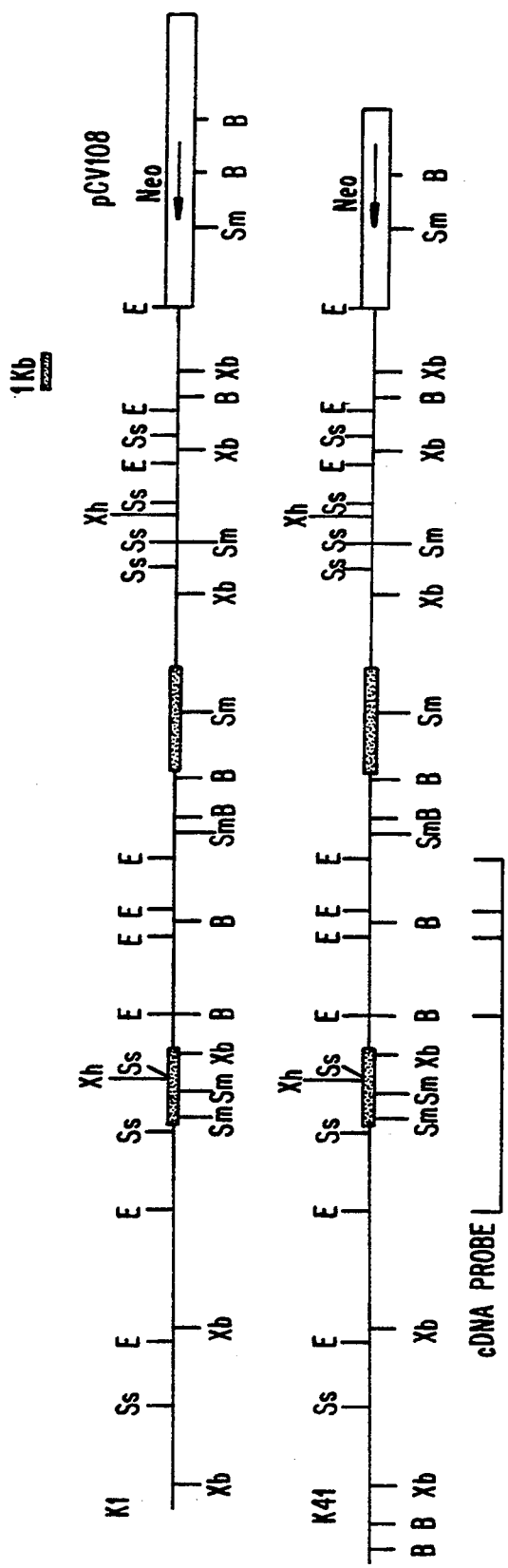
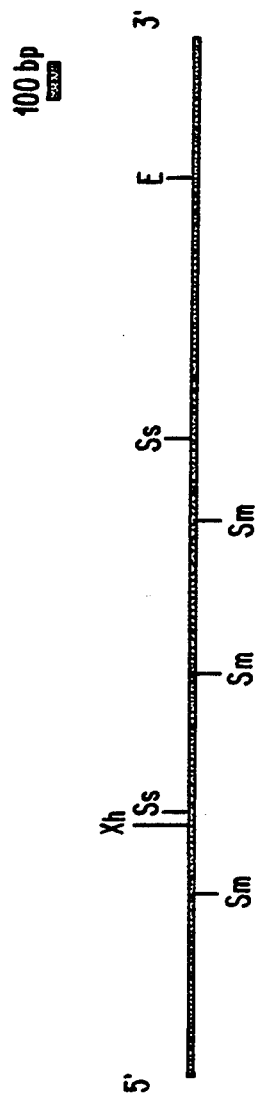
FIG. 1A.
FIG. 1B.

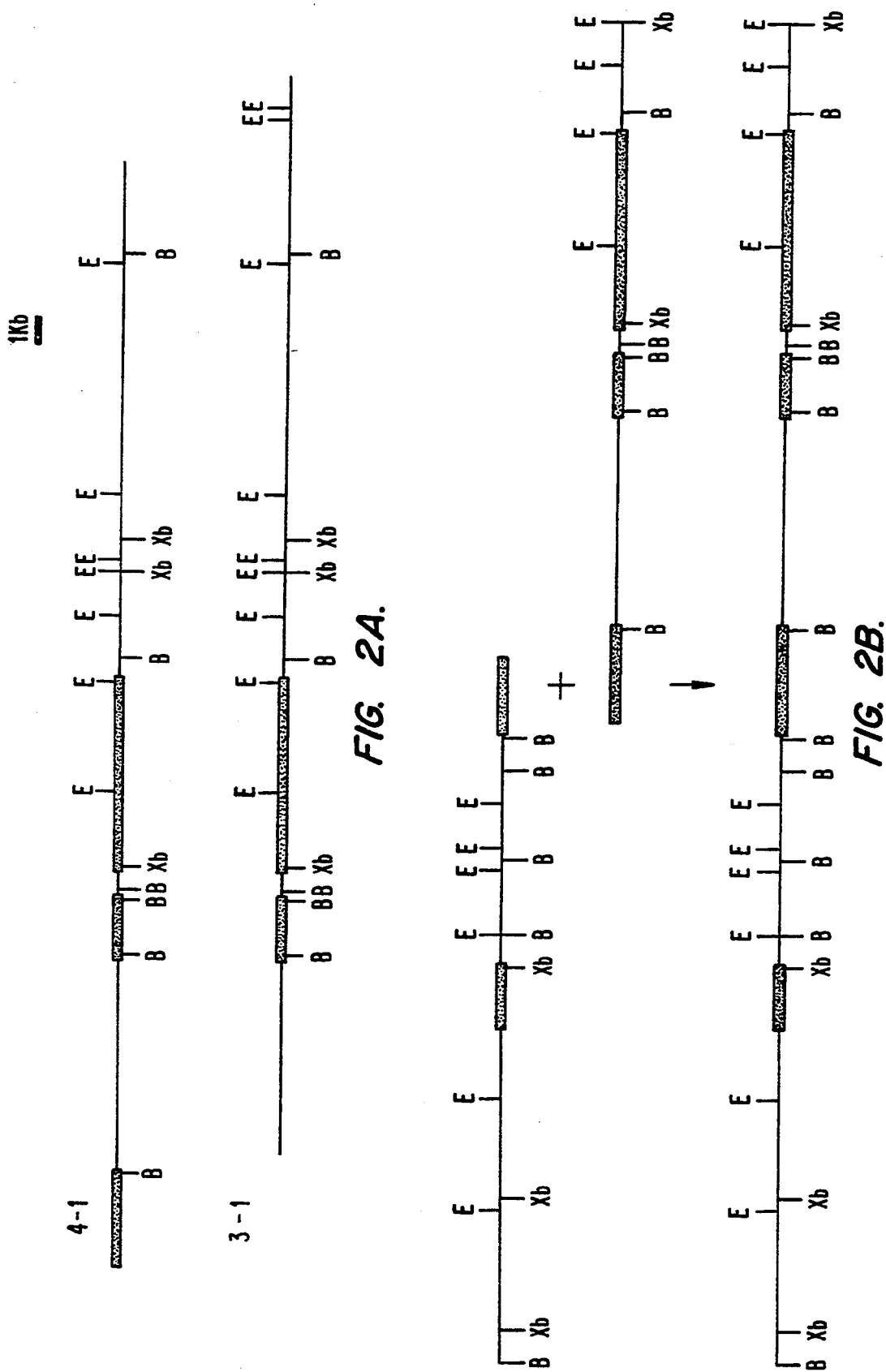

```
   1    CTCCTCACAG GTGTGTCTCT AGTCCTCGTG GTTGCCTGCC CCACTCCCTG
  51    CCGAGACGCC TGCCAGAAAG GTCACCTATC CTGAACCCCA GCAAGCCTGA
                                      START      Pst I
 101    AACAGCTCAG CCAAGCACCC TGCG ATG GAA GCTGCAGATG CCTCCAGGAG
 151    CAACGGGTCG AGCCCAGAAG CCAGGGATGC CCGGAGCCCG TCGGGCCCCA
 201    GTGGCAGCCT GGAGAATGGC ACCAAGGCTG ACGGCAAGGA TGCCAAGACC
 251    ACCAACGGGC ACGGCGGGGA GGCAGCTGAG GGCAAGAGCC TGGGCAGCGC
 301    CCTGAAGCCA GGGGAAGGTA GGAGCGCCCT GTTCGCGGGC AATGAGTGGC
 351    GGCGACCCAT CATCCAGTTT GTCGAGTCCG GGACGACAA GAACTCCAAC
 401    TACTTCAGCA TGGACTCTAT GGAAGGCAAG AGGTCGCCGT ACGCAGGGCT
          Pvu I
 451    CCAGCTGGGG GCTGCCAAGA AGCCACCCGT TACCTTTGCC GAAAAGGGCG
 501    ACGTGCGCAA GTCCATTTTC TCGGAGTCCC GGAAGCCCAC GGTGTCCATC
                   Sma I                              Sma I
 551    ATGGAGCCCG GGAGACCCG GCGGAACAGC TACCCCGGG CCGACACGGG
 601    CCTTTTTTCA CGGTCCAAGT CCGGCTCCGA GGAGGTGCTG TGCGACTCCT
 651    GCATCGGCAA CAAGCAGAAG GCGGTCAAGT CCTGCCTGGT GTGCCAGGCC
 701    TCCTTCTGCG AGCTGCATCT CAAGCCCCAC CTGGAGGGCG CCGCCTTCCG
                          Xho I
 751    AGACCACCAG CTGCTCGAGC CCATCCGGGA CTTTGAGGCC GGCAAGTGTC
                          Sst I
 801    CCGTGCATGG CAAGACGATG GAGCTCTTCT GCCAGACCGA CCAGACCTGC
 851    ATCTGCTACC TTTGCATGTT CCAGGAGCAC AAGAATCATA GCACCGTGAC
                                        EXON 1 EXON 2
 901    AGTGGAGGAG GCCAAGGCCG AGAAGGAG AC GGAGCTGTCA CTGCAAAAGG
          Pvu I Pst I
 951    AGCAGCTGCA GCTCAAGATC ATTGAGATTG AGGATGAAGC TGAGAAGTGG
                                      EXON 2 EXON 3
1001    CAGAAGGAGA AGGACCGCAT CAAG AGCTTC ACCACCAATG AGAAGGCCAT
1051    CCTGGAGCAG AACTTCCGGG ACCTGGTGCG GGACCTGGAG AAGCAAAAGG
1101    AGGAAGTGAG GGCTGCGCTG GAGCAGCGGG AGCAGGATGC TGTGGACCAA
1151    GTGAAGGTGA TCATGGATGC TCTGGATGAG AGAGCCAAGG TGCTGCATGA
                   Sma I
1201    GGACAAGCAG ACCCGGGAGC AGCTGCATAG CATCAGCGAC TCTGTGTTGT
        EXON 3 EXON 4
1251    TTCTGCAG GA ATTTGGTGCA TTGATGAGCA ATTACTCTCT CCCCCCACCC
          Pst I
1301    CTGCCCACCT ATCATGTCCT GCTGGAGGGG GAGGGCCTGG GACAGTCACT
```

*FIG. 6A.*

```
1351  AGGCAACTTC AAGGACGACC TGCTCAATGT ATGCATGCGC CACGTTGAGA
1401  AGATGTGCAA GGCGGACCTG AGCCGTAACT TCATTGAGAG GAACCACATG
           EXON4|EXON 5
1451  GAGAACG|GTG GTGACCATCG CTATGTGAAC AACTACACGA ACAGCTTCGG
1501  GGGTGAGTGG AGTGCACCGG ACACCATGAA GAGATACTCC ATGTACCTGA
           EXON5|EXON 6
1551  CACCCAAAG|G TGGGGTCCGG ACATCATACC AGCCCTCGTC TCCTGGCCGC
1601  TTCACCAAGG AGACCACCCA GAAGAATTTC AACAATCTCT ATGGCACCAA
           EXON6|EXON7        SmaI
1651  AG|GTAACTAC ACCTCCCGGG TCTGGGAGTA CTCCTCCAGC ATTCAGAACT
1701  CTGACAATGA CCTGCCCGTC GTCCAAGGCA GCTCCTCCTT CTCCCTGAAA
           EXON7|EXON8
1751  G|GCTATCCCT CCCTCATGCG GAGCCAAAGC CCAAGGCCC AGCCCAGAC
                                            EXON8|EXON9
1801  TTGGAAATCT GGCAAGCAGA CTATGCTG|TC TCACTACCGG CCATTCTACG
                                            STOP    SstI
1851  TCAACAAAGG CAACGGGATT GGGTCCAACG AAGCCCCATG AGCTCCTGGC
1901  GGAAGGAACG AGGCGCCACA CCCCTGCTCT TCCTCCTGAC CCTGCTGCTC
1951  TTGCCTTCTA AGCTACTGTG CTTGTCTGGG TGGAGGGAG CCTGGTCCTG
                  Pst I
2001  CACCTGCCCT CTGCAGCCCT CTGCCAGCCT CTTGGGGGCA GTTCCGGCCT
2051  CTCCGACTTC CCCACTGGCC ACACTCCATT CAGACTCCTT TCCTGCCTTG
2101  TGACCTCAGA TGGTCACCAT CATTCCTGTG CTCAGAGGCC AACCCATCAC
2151  AGGGGTGAGA TAGGTTGGGG CCTGCCCTAA CCCGCCAGCC TCCTCCTCTC
2201  GGGCTGGATC TGGGGGCTAG CAGTGAGTAC CCGCATGGTA TCAGCCTGCC
2251  TCTCCCGCCC ACGCCCTGCT GTCTCCAGGC CTATAGACGT TTCTCTCCAA
2301  GGCCCTATCC CCCAATGTTG TCAGCAGATG CCTGGACAGC ACAGCCACCC
2351  ATCTCCCATT CACATGGCCC ACCTCCTGCT TCCCAGAGGA CTGGCCCTAC
                                                              PstI
2401  GTGCTCTCTC TCGTCCTACC TATCAATGCC CAGCATGGCA GAACCTGCAG
              PstI
2451  TGGCCAAGGG CTGCAGATGG AAACCTCTCA GTGTCTTGAC ATCACCCTAC
2501  CCAGGCGGTG GGTCTCCACC ACAGCCACTT TGAGTCTGTG GTCCCTGGAG
2551  GGTGGCTTCT CCTGACTGGC AGGATGACCT TAGCCAAGAT ATTCCTCTGT
                                      EcoRI
2601  TCCCTCTGCT GAGATAAAGA ATTCCCTTAA CATGATATAA TCCACCCATG
2651  CAAATAGCTA CTGGCCCAGC TACCATTTAC CATTTGCCTA CAGAATTTCA
```

FIG. 6B.

```
2701   TTCAGTCTAC ACTTTGGCAT TCTCTCTGGC GATGGAGTGT GGCTGGGCTG
2751   ACCGCAAAAG GTGCCTTACA CACTGCCCCC ACCCTCAGCC GTTGCCCCAT
2801   CAGAGGCTGC CTCCTCCTTC TGATTACCCC CCATGTTGCA TATCAGGGTG
2851   CTCAAGGATT GGAGAGGAGA CAAAACCAGG AGCAGCACAG TGGGACATC
2901   TCCCGTCTCA ACAGCCCCAG GCCTATGGGG GCTCTGGAAG GATGGGCCAG
2951   CTTGCAGGGG TTGGGGAGGG AGACATCCAG CTTGGGCTTT CCCCTTTGGA
       POLY A ADDITION SEQUENCE
3001   ATAAACCATT GGTCTGTC - POLY A
```

*FIG. 6C.*

```
  1                                21                                  41
  ATG GAA GCT GCA GAT GCC TCC AGG AGC AAC GGG TCG AGC CCA GAA
1: met glu ala ala asp ala ser arg ser asn gly ser ser pro glu 61                                  81
  GCC AGG GAT GCC CGG AGC CCG TCG GGC CCC AGT GGC AGC CTG GAG
1: ala arg asp ala arg ser pro ser gly pro ser gly ser leu glu 101                                 121
  AAT GGC ACC AAG GCT GAC GGC AAG GAT GCC AAG ACC ACC AAC GGG
1: asn gly thr lys ala asp gly lys asp ala lys thr thr asn gly 141                           161
  CAC GGC GGG GAG GCA GCT GAG GGC AAG AGC CTG GGC AGC GCC CTG
1: his gly gly glu ala ala glu gly lys ser leu gly ser ala leu 181                           201                           221
  AAG CCA GGG GAA GGT AGG AGC GCC CTG TTC GCG GGC AAT GAG TGG
1: lys pro gly glu gly arg ser ala leu phe ala gly asn glu trp 241                                 261
  CGG CGA CCC ATC ATC CAG TTT GTC GAG TCC GGG GAC GAC AAG AAC
1: arg arg pro ile ile gln phe val glu ser gly asp asp lys asn 281                                 301
  TCC AAC TAC TTC AGC ATG GAC TCT ATG GAA GGC AAG AGG TCG CCG
1: ser asn tyr phe ser met asp ser met glu gly lys arg ser pro 321                           341
  TAC GCA GGG CTC CAG CTG GGG GCT GCC AAG AAG CCA CCC GTT ACC
1: tyr ala gly leu gln leu gly ala ala lys lys pro pro val thr 361                           381                           401
  TTT GCC GAA AAG GGC GAC GTG CGC AAG TCC ATT TTC TCG GAG TCC
1: phe ala glu lys gly asp val arg lys ser ile phe ser glu ser 421                                 441
  CGG AAG CCC ACG GTG TCC ATC ATG GAG CCC GGG GAG ACC CGG CGG
1: arg lys pro thr val ser ile met glu pro gly glu thr arg arg
```

*FIG. 7A.*

```
        461                                    481
    AAC AGC TAC CCC CGG GCC GAC ACG GGC CTT TTT TCA CGG TCC AAG
1:  asn ser tyr pro arg ala asp thr gly leu phe ser arg ser lys 501                                    521
    TCC GGC TCC GAG GAG GTG CTG TGC GAC TCC TGC ATC GGC AAC AAG
1:  ser gly ser glu glu val leu cys asp ser cys ile gly asn lys 541                       561                           581
    CAG AAG GCG GTC AAG TCC TGC CTG GTG TGC CAG GCC TCC TTC TGC
1:  gln lys ala val lys ser cys leu val cys gln ala ser phe cys 601                    621
    GAG CTG CAT CTC AAG CCC CAC CTG GAG GGC GCC GCC TTC CGA GAC
1:  glu leu his leu lys pro his leu glu gly ala ala phe arg asp 641                            661
    CAC CAG CTG CTC GAG CCC ATC CGG GAC TTT GAG GCC CGC AAG TGT
1:  his gln leu leu glu pro ile arg asp phe glu ala arg lys cys 681                        701
    CCC GTG CAT GGC AAG ACG ATG GAG CTC TTC TGC CAG ACC GAC CAG
1:  pro val his gly lys thr met glu leu phe cys gln thr asp gln 721                            741                       761
    ACC TGC ATC TGC TAC CTT TGC ATG TTC CAG GAG CAC AAG AAT CAT
1:  thr cys ile cys tyr leu cys met phe gln glu his lys asn his 781                       801
    AGC ACC GTG ACA GTG GAG GAG GCC AAG GCC GAG AAG GAG ACG GAG
1:  ser thr val thr val glu glu ala lys ala glu lys glu thr glu 821                            841
    CTG TCA CTG CAA AAG GAG CAG CTG CAG CTC AAG ATC ATT GAG ATT
1:  leu ser leu gln lys glu gln leu gln leu lys ile ile glu ile 861                        881
    GAG GAT GAA GCT GAG AAG TGG CAG AAG GAG AAG GAC CGC ATC AAG
1:  glu asp glu ala glu lys trp gln lys glu lys asp arg ile lys
```

*FIG. 7B.*

```
        901                         921                         941
    AGC TTC ACC ACC AAT GAG AAG GCC ATC CTG GAG CAG AAC TTC CGG
 1: ser phe thr thr asn glu lys ala ile leu glu gln asn phe arg 961                         981
    GAC CTG GTG CGG GAC CTG GAG AAG CAA AAG GAG GAA GTG AGG GCT
 1: asp leu val arg asp leu glu lys gln lys glu glu val arg ala 1001                         1021
    GCG CTG GAG CAG CGG GAG CAG GAT GCT GTG GAC CAA GTG AAG GTG
 1: ala leu glu gln arg glu gln asp ala val asp gln val lys val 1041                         1061
    ATC ATG GAT GCT CTG GAT GAG AGA GCC AAG GTG CTG CAT GAG GAC
 1: ile met asp ala leu asp glu arg ala lys val leu his glu asp 1081                         1101                         1121
    AAG CAG ACC CGG GAG CAG CTG CAT AGC ATC AGC GAC TCT GTG TTG
 1: lys gln thr arg glu gln leu his ser ile ser asp ser val leu 1141                         1161
    TTT CTG CAG GAA TTT GGT GCA TTG ATG AGC AAT TAC TCT CTC CCC
 1: phe leu gln glu phe gly ala leu met ser asn tyr ser leu pro 1181                         1201
    CCA CCC CTG CCC ACC TAT CAT GTC CTG CTG GAG GGG GAG GGC CTG
 1: pro pro leu pro thr tyr his val leu leu glu gly glu gly leu 1221                         1241
    GGA CAG TCA CTA GGC AAC TTC AAG GAC GAC CTG CTC AAT GTA TGC
 1: gly gln ser leu gly asn phe lys asp asp leu leu asn val cys 1261                         1281                         1301
    ATG CGC CAC GTT GAG AAG ATG TGC AAG GCG GAC CTG AGC CGT AAC
 1: met arg his val glu lys met cys lys ala asp leu ser arg asn 1321                         1341
    TTC ATT GAG AGG AAC CAC ATG GAG AAC GGT GGT GAC CAT CGC TAT
 1: phe ile glu arg asn his met glu asn gly gly asp his arg tyr
```

*FIG. 7C.*

```
         1361                          1381
   GTG AAC AAC TAC ACG AAC AGC TTC GGG GGT GAG TGG AGT GCA CCG
1: val asn asn tyr thr asn ser phe gly gly glu trp ser ala pro 1401                          1421
   GAC ACC ATG AAG AGA TAC TCC ATG TAC CTG ACA CCC AAA GGT GGG
1: asp thr met lys arg tyr ser met tyr leu thr pro lys gly gly 1441                     1461                      1481
   GTC CGG ACA TCA TAC CAG CCC TCG TCT CCT GGC CGC TTC ACC AAG
1: val arg thr ser tyr gln pro ser ser pro gly arg phe thr lys 1501                         1521
   GAG ACC ACC CAG AAG AAT TTC AAC AAT CTC TAT GGC ACC AAA GGT
1: glu thr thr gln lys asn phe asn asn leu tyr gly thr lys gly 1541                       1561
   AAC TAC ACC TCC CGG GTC TGG GAG TAC TCC TCC AGC ATT CAG AAC
1: asn tyr thr ser arg val trp glu tyr ser ser ser ile gln asn 1581                      1601
   TCT GAC AAT GAC CTG CCC GTC GTC CAA GGC AGC TCC TCC TTC TCC
1: ser asp asn asp leu pro val val gln gly ser ser ser phe ser 1621                     1641                      1661
   CTG AAA GGC TAT CCC TCC CTC ATG CGG AGC CAA AGC CCC AAG GCC
1: leu lys gly tyr pro ser leu met arg ser gln ser pro lys ala 1681                       1701
   CAG CCC CAG ACT TGG AAA TCT GGC AAG CAG ACT ATG CTG TCT CAC
1: gln pro gln thr trp lys ser gly lys gln thr met leu ser his 1721                       1741
   TAC CGG CCA TTC TAC GTC AAC AAA GGC AAC GGG ATT GGG TCC AAC
1: tyr arg pro phe tyr val asn lys gly asn gly ile gly ser asn 1761
   GAA GCC CCA TGA
1: glu ala pro ***
```

FIG. 7D.

| FRAGMENT | PRIMER | SEQUENCE |
|---|---|---|
| 1A | 1A-5 | TCTCTAGTCCTCGTGGTT |
|    | 1A-3 | GGTGGTCTTGGCATCCTT |
| 1B | 1B-5 | TGGAGAATGGCACCAAGG |
|    | 1B-3 | TCCATGATGGACACCGTG |
| 1C | 1C-5 | TCTATGGAAGGCAAGAGG |
|    | 1C-3 | GGAGAAGATGAAGTTCGG |
| 2  | 2-5  | TGACTTCTCCAATCCTGG |
|    | 2-3  | CCTGGACTCAAATGGGAG |
| 3  | 3-5  | AAGACATACCCGACTAGG |
|    | 3-3  | TGTGAAATCGAGGGCTTG |
| 4  | 4-5  | AGCGTCCTCATAGCTCAT |
|    | 4-3  | TGAGAAGAAGCTCACTGG |
| 5  | 5-5  | AAACTTGGATCTGCCTGG |
|    | 5-3  | AGTCACTGCACGGACTTT |
| 6  | 6-5  | GAGTCCTGATGAGACAAT |
|    | 6-3  | CATTCATCTCACACTGGG |
| 7  | 7-5  | AGAGAGTCATAGACCTGG |
|    | 7-3  | GAGGAACTAGCAGCTCAG |
| 8  | 8-5  | GACGGCTGCATTTGGTAA |
|    | 8-3  | CAGAGAAGTCCTCCCACA |
| 9A | 9A-5 | AGAATTGTCGGGTCTTGG |
|    | 9A-3 | GCACAGTAGCTTAGAAGG |
| 9B | 9B-5 | ACAAAGGCAACGGGATTG |
|    | 9B-3 | TCTGCTGACAACATTGGG |
| 9C | 9C-5 | AGACGTTTCTCTCCAAGG |
|    | 9C-3 | CTTTATCTCAGCAGAGGG |
| 9D | 9D-5 | AGGATGACCTTAGCCAAG |
|    | 9D-3 | GAAGAACTGCAGCCTGTT |

*FIG. 9.*

1A
(SEQUENCED STRAND)

```
         1A-5
1    TCTCTAGTCCTCGTGGTTGCCTGCCCCACTCCCTGCCGAG

41   ACGCCTGCCAGAAAGGTCACCTATCCTGAACCCCAGCAAG
                                    START      PstI
81   CCTGAAACAGCTCAGCCAAGCACCCTGCGATGGAAGCTGC

121  AGATGCCTCCAGGAGCAACGGGTCGAGCCCAGAAGCCAGG

161  GATGCCGGAGCCCGTCGGGCCCCAGTGGCAGCCTGGAGA

201  ATGGCACCAAGGCTGACGGCAAGGATGCCAAGACCACC
                                        1A-3
```

FIG. 10A.

1B
(SEQUENCED STRAND)

```
         1B-5
1    TGGAGAATGGCACCAAGGCTGACGGCAAGGATGCCAAGAC

41   CACCAACGGGCACGGCGGGGAGGCAGCTGAGGGCAAGAGC

81   CTGGGCAGCGCCCTGAAGCCAGGGGAAGGTAGGAGCGCCC

121  TGTTCGCGGGCAATGAGTGGCGGCGACCCATCATCCAGTT

161  TGTCGAGTCCGGGGACGACAAGAACTCCAACTACTTCAGC

201  ATGGACTCTATGGAAGGCAAGAGGTCGCCGTACGCAGGGC
           PvuI
241  TCCAGCTGGGGGCTGCCAAGAAGCCACCCGTTACCTTTGC

281  CGAAAAGGGCGACGTGCGCAAGTCCATTTTCTCGGAGTCC

321  CGGAAGCCCACGGTGTCCATCATGGA
              1B-3
```

FIG. 10B.

1C
(SEQUENCED STRAND)

```
          IC-5
  1   TCTATGGAAGGCAAGAGGTCGCCGTACGCAGGGCTCCAGC

41   TGGGGGCTGCCAAGAAGCCACCCGTTACCTTTGCCGAAAA

81   GGGCGACGTGCGCAAGTCCATTTTCTCGGAGTCCCGGAAG
                                   Sma I
121   CCCACGGTGTCCATCATGGAGCCCGGGGAGACCCGGCGGA
             Sma I
161   ACAGCTACCCCCGGGCCGACACGGGCCTTTTTTCACGGTC

201   CAAGTCCGGCTCCGAGGAGGTGCTGTGCGACTCCTGCATC

241   GGCAACAAGCAGAAGGCGGTCAAGTCCTGCCTGGTGTGCC

281   AGGCCTCCTTCTGCGAGCTGCATCTCAAGCCCCACCTGGA
                                    Xho I
321   GGGCGCCGCCTTCCGAGACCACCAGCTGCTCGAGCCCATC

361   CGGGACTTTGAGGCCCGCAAGTGTCCCGTGCATGGCAAGA
             Sst I
401   CGATGGAGCTCTTCTGCCAGACCGACCAGACCTGCATCTG

441   CTACCTTTGCATGTTCCAGGAGCACAAGAATCATAGCACC
                                  EXON 1 | INTRON
481   GTGACAGTGGAGGAGGCCAAGGCCGAGAAGGAG|GTAAGTG

521   CTGGGGCCCCTCCTGCCCCTCCAGGCCTCTCCTCTCTCAA

561   CCCACCCCTCCGAACTTCATCTTCTCC
                  IC-3
```

FIG. 10C.

2
(SEQUENCED STRAND)

```
        2-5                         INTRON  EXON2
1   TGACTTCTCCAATCCTGGCTCTTTCT CTGCAG ACGGAGCT
                                PstI   PstI
41  GTCACTGCAAAAGGAGCAG CTGCAG CTCAAGATCATTGAG

81  ATTGAGGATGAAGCTGAGAAGTGGCAGAAGGAGAAGGACC
       EXON 2  INTRON
121 GCATCAAG GTGAGCAGCCCCCAAGCTCACCTTGCTGCTCC

161 CTTACCCGACCTGGCCTGCCTGGAAAGACGCAGGCCTTGG

201 CTCCCATTTGAGTCCAGG
            2-3
```

FIG. 10D.

3
(SEQUENCED STRAND)

```
         3-5
1   AAGACATACCCGACTAGGGTGATTTCTTTCCCTAACTAAA
                                     INTRON EXON3
41  GCCCTGCCTAATCTCTTCCCTGACTCTGGACCTCCAG AGC

81  TTCACCACCAATGAGAAGGCCATCCTGGAGCAGAACTTCC

121 GGGACCTGGTGCGGGACCTGGAGAAGCAAAAGGAGGAAGT

161 GAGGGCTGCGCTGGAGCAGCGGGAGCAGGATGCTGTGGAC

201 CAAGTGAAGGTGATCATGGATGCTCTGGATGAGAGAGCCA

241 AGGTGCTGCATGAGGACAAGCAGACCCGGGAGCAGCTGCA
                                  EXON3  INTRON
281 TAGCATCAGCGACTCTGTGTTGTTTCTGCAG GTAACAAGC

321 CACTCCTCTGTCACTCAAGCCCTCGATTTCACA
                          3-3
```

FIG. 10E.

4
(SEQUENCED STRAND)

4-5
1    AGCGTCCTCATAGCTCATGAAGACCCAGGCAGTTAATGGT
                       INTRON, EXON 4
41   TCTTTCCTTTCTTGGTAG|GAATTTGGTGCATTGATGAGCA

81   ATTACTCTCTCCCCCACCCCTGCCCACCTATCATGTCCT

121  GCTGGAGGGGGAGGGCCTGGGACAGTCACTAGGCAACTTC

161  AAGGACGACCTGCTCAATGTATGCATGCGNCACGTTGAGA

201  AGATGTGCAAGGCGNACCTGAGCNGTAACTTCATTGAGAG
                EXON 4, INTRON
241  GAACCACATGGAGAACG|GTAGGTCCCCTCTCGTGGCTGGG

281  CCCCAAGGCNATAGACCTTTCTCTCCAAATCAATTCCTG

321  CTGCCTGACATGGGCTGGCCTCCAGTGAGCTTCTTCTCA
                                    4-3

FIG. 10F.

5
(SEQUENCED STRAND)

5-5
1    AAACTTGGATCTGCCTGGGAGATAGGGGAAGGGCTATGGG

41   GTGACTCATCTGAGCCCCAAAAGTCCCCAGTGGCTGGCTC

81   CTCCTTCCCACCTGGCTCCTCTGCTGACCCGACCCTCTGC
        INTRON, EXON 5
121  TTCCTAG|GTGGTGACCATCGCTATGTGAACAACTACACGA

161  ACAGCTTCGGGGGTGAGTGGAGTGCACCGGACACCATGAA
                              EXON 5, INTRON
201  GAGATACTCCATGTACCTGACACCCAAAG|GTAAGAGGGAG

241  CCCCTCACCCCAGACCTAGTGTCTCTCCTGCTGCCCAGGG

281  GCCCCCAAAGTCCGTGCAGTGACT
            5-3

FIG. 10G.

6
(SEQUENCED STRAND)

```
         6-5
  1  GAGTCCTGATGAGACAATTTTGTGCAATGACAGCCCNNTT
              INTRON| EXON6
 41  CATCTGCTTCACAG|GTGGGGTCCGGACATCATACCAGCCC

81  TCGTCTCCTGGCCGCTTCACCAAGGAGACCACCCAGAAGA
                            EXON6| INTRON
121  ATTTCAACAATCTCTATGGCACCAAAG|NNNNNNNNTGGGNC

161  TGTGCAGGCAGGAGGGCATAGAGGTGGGTCCAGNGGCACA

201  GGGCTGGGACCCCAGTGTGAGATGAATG
                   6-3
```

FIG. 10H.

7
(SEQUENCED STRAND)

```
         7-5
  1  AGAGAGTCATAGACCTGGCTGTGTCCTGGTCCTGCCTCCT

41  CTCCCACTCCCAGCTGTGGGGGCCTGACAGCCCTTCTTTG
         INTRON | EXON7        SmaI
 81  TCCTGCCAG|GTAACTACACCTCCCGGGTCTGGGAGTACTC

121  CTCCAGCATTCAGAACTCTGACAATGACCTGCTGTCGTCC
                              EXON 7 | INTRON
161  AAGGCAGCTCCTCCTTCTCCCTGAAAG|GTGAGCCCTGCCC

201  ACCCTGGCCCCTGCTTTCCTCCACAGCTGCCTCACACCTC

241  CCAAGCCCTGCTTGGGTCTCTTCGCTGAGCTGCTAGTTCC
                                          7-3
281  TC
```

FIG. 10I.

8
(SEQUENCED STRAND)

```
           8-5
  1    GACGGCTGCATTTGGTAATGGGCTGGATGATGCTTGGTGG

41    TACACTTTGGAGAAGNAGCTGTGCTGCTCTGGGNCCGGGN

81    NCCCCTGGCCNNNNNNNNNNNNNNNNNNNNNNNNNNNN
              INTRON | EXON 8
121    NNNNNNNNNNNN|GCTATCCCTCCCTCATGCGGAGCCAAAG

161    CCCCAAGGCCCAGCCCCAGACTTGGAAATCTGGCAAGCAG
           EXON 8 | INTRON
201    ACTATGCTG|GTAAGGGAAGTGCGGCCGGGAGGGCCTGGGC

241    ACATCCAGAGACCTGGGCACTGAAGGGGGCTCCCTGGAGG

281    CAATCGGTTCCAGGGCCTGTGGGAGGACTTCTCTG
                                  8-3
```

FIG. 10J.

9A
(UNSEQUENCED STRAND)

```
          9A-5
  1    AGAATTGTCGGGTCTTGGATCACTGCTGCCTCCTGAGGCA

41    GGTTAGGGTAGGGTGGGTCTAGCTAGCAGGCTCATCTGTC
                                   INTRON | EXON 9
 81    GTCTGGCCTCGCTGACCACTCTTGTTTCCCCACAG|TCTC

121    ACTACCGGCCATTCTACGTCAACAAAGGCAACGGGATTGG
                         STOP SstI
161    GTCCAACGAAGCCCCA|TGA|GCTCCTGGCGGAAGGAACGAG

201    GCGCCACACCCCTGCTCTTCCTCCTGACCCTGCTGCTCTT

241    GCCTTCTAAGCTACTGTGC
           9A-3
```

FIG. 10K.

9B
(SEQUENCED STRAND)

```
           9B-5
   1   ACAAAGGCAACGGGATTGGGTCCAACGAAGCCCCATGAGC

41   TCCTGGCGGAAGGAACGAGGCGCCACACCCCTGCTCTTCC

81   TCCTGACCCTGCTGCTCTTGCCTTCTAAGCTACTGTGCTT
                                             PstI
 121   GYCTGGGTGGGAGGGAGCCTGGTCCTGCACCTGCCCTCTG

161   CAGCCCTCTGCCAGCCTCTTGGGGCAGTTCCGGCCTCTC

201   CGACTTCCCCACTGGCCACACTCCATTCAGACTCCTTTCC

241   TGCCTTGTGACCTCAGATGGTCACCATCATTCCTGTGCTC

281   AGAGGCCAACCCATCACAGGGGTGAGATAGGTTGGGGCCT

321   GCCCTAACCCGCCAGCCTCCTCCTCTCGGGCTGGATCTGG

361   GGGCTAGCAGTGAGTACCCGCATGGTATCAGCCTGCCTCT

401   CCCGCCCACGCCCTGCTGTCTCCAGGCCTATAGACGTTTC

441   TCTCCAAGGCCCTATCCCCCAATGTTGTCAGCAGA
                             9B-3
```

FIG. 10L.

9C
(SEQUENCED STRAND)

9C-5

1   AGACGTTTCTCTCCAAGGCCCTATCCCCCAATGTTGTCAG

41  CAGATGCCTGGACAGCACAGCCACCCATCTCCCATTCACA

81  TGGCCCACCTCCTGCTTCCCAGAGGACTGGCCCTACGTGC

121 TCTCTCTCGTCCTACCTATCAATGCCCAGCATGGCAGAAC

Pst I        Pst I
161 CTGCAGTGGCCAAGGGCTGCAGATGGAAACCTCTCAGTGT

201 CTTGACATCACCCTACCCAGGCGGTGGGTCTCCACCACAG

241 CCACTTTGAGTCTGTGGTCCCTGGAGGGTGGCTTCTCCTG

281 ACTGGCAGGATGACCTTAGCCAAGATATTCCTCTGTTCCC

321 TCTGCTGAGATAAAG 9C-3

*FIG. 10M.*

9D
(SEQUENCED STRAND)

<u>          9D-5          </u>

1    AGGATGACCTTAGCCAAGATATTCCTCTGTTCCCTCTGCT

EcoRI

41    GAGATAAA<u>GAATTC</u>CCTTAACATGATATAATCCACCCATG

81    CAAATAGCTACTGGCCCAGCTACCATTTACCATTTGCCTA

121    CAGAATTTCATTCAGTCTACACTTTGGCATTCTCTCTGGC

151    GATGGAGTGTGGCTGGGCTGACCGCAAAAGGTGCCTTACA

201    CACTGCCCCACCCTCAGCCGTTGCCCCATCAGAGGCTGC

241    CTCCTCCTTCTGATTACCCCCATGTTGCATATCAGGGTG

281    CTCAAGGATTGGAGAGGAGACAAAACCAGGAGCAGCACAG

321    TGGGACATCTCCCGTCTCAACAGCCCCAGGCCTATGGGG

361    GCTCTGGAAGGATGGGCCAGCTTGCAGGGGTTGGGGAGGG

401    AGACATCCAGCTTGGGCTTTCCCCTTTGGAATAAACCATT cDNA - END

441    GGTCTGTCACTTCTCTTGTATTGAATGACCATTTCCCTGA

481    GGGTCCCCAGAGG<u>AACAGGCTGCAGTTCTTC</u>

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 3018 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

-continued

```
CTCCTCACAG GTGTGTCTCT AGTCCTCGTG GTTGCCTGCC CCACTCCCTG CCGAGACGCC     60
TGCCAGAAAG GTCACCTATC CTGAACCCCA GCAAGCCTGA AACAGCTCAG CCAAGCACCC    120
TGCGATGGAA GCTGCAGATG CCTCCAGGAG CAACGGGTCG AGCCCAGAAG CCAGGGATGC    180
CCGGAGCCCG TCGGGCCCCA GTGGCAGCCT GGAGAATGGC ACCAAGGCTG ACGGCAAGGA    240
TGCCAAGACC ACCAACGGGC ACGGCGGGGA GGCAGCTGAG GGCAAGAGCC TGGGCAGCGC    300
CCTGAAGCCA GGGGAAGGTA GGAGCGCCCT GTTCGCGGGC AATGAGTGGC GGCGACCCAT    360
CATCCAGTTT GTCGAGTCCG GGACGACAA GAACTCCAAC TACTTCAGCA TGGACTCTAT    420
GGAAGGCAAG AGGTCGCCGT ACGCAGGGCT CCAGCTGGGG GCTGCCAAGA AGCCACCCGT    480
TACCTTTGCC GAAAAGGGCG ACGTGCGCAA GTCCATTTTC TCGGAGTCCC GGAAGCCCAC    540
GGTGTCCATC ATGGAGCCCG GGAGACCCG GCGGAACAGC TACCCCCGGG CCGACACGGG    600
CCTTTTTTCA CGGTCCAAGT CCGGCTCCGA GGAGGTGCTG TGCGACTCCT GCATCGGCAA    660
CAAGCAGAAG GCGGTCAAGT CCTGCCTGGT GTGCCAGGCC TCCTTCTGCG AGCTGCATCT    720
CAAGCCCCAC CTGGAGGGCG CCGCCTTCCG AGACCACCAG CTGCTCGAGC CCATCCGGGA    780
CTTTGAGGCC CGCAAGTGTC CCGTGCATGG CAAGACGATG GAGCTCTTCT GCCAGACCGA    840
CCAGACCTGC ATCTGCTACC TTTGCATGTT CCAGGAGCAC AAGAATCATA GCACCGTGAC    900
AGTGGAGGAG GCCAAGGCCG AGAAGGAGAC GGAGCTGTCA CTGCAAAAGG AGCAGCTGCA    960
GCTCAAGATC ATTGAGATTG AGGATGAAGC TGAGAAGTGG CAGAAGGAGA AGGACCGCAT   1020
CAAGAGCTTC ACCACCAATG AGAAGGCCAT CCTGGAGCAG AACTTCCGGG ACCTGGTGCG   1080
GGACCTGGAG AAGCAAAAGG AGGAAGTGAG GGCTGCGCTG GAGCAGCGGG AGCAGGATGC   1140
TGTGGACCAA GTGAAGGTGA TCATGGATGC TCTGGATGAG AGAGCCAAGG TGCTGCATGA   1200
GGACAAGCAG ACCCGGGAGC AGCTGCATAG CATCAGCGAC TCTGTGTTGT TTCTGCAGGA   1260
ATTTGGTGCA TTGATGAGCA ATTACTCTCT CCCCCCACCC CTGCCCACCT ATCATGTCCT   1320
GCTGGAGGGG GAGGGCCTGG GACAGTCACT AGGCAACTTC AAGGACGACC TGCTCAATGT   1380
ATGCATGCGC CACGTTGAGA AGATGTGCAA GGCGGACCTG AGCCGTAACT TCATTGAGAG   1440
GAACCACATG GAGAACGGTG GTGACCATCG CTATGTGAAC AACTACACGA ACAGCTTCGG   1500
GGGTGAGTGG AGTGCACCGG ACACCATGAA GAGATACTCC ATGTACCTGA CACCCAAAGG   1560
TGGGGTCCGG ACATCATACC AGCCCTCGTC TCCTGGCCGC TTCACCAAGG AGACCACCCA   1620
GAAGAATTTC AACAATCTCT ATGGCACCAA AGGTAACTAC ACCTCCCGGG TCTGGGAGTA   1680
CTCCTCCAGC ATTCAGAACT CTGACAATGA CCTGCCCGTC GTCCAAGGCA GCTCCTCCTT   1740
CTCCCTGAAA GGCTATCCCT CCCTCATGCG GAGCCAAAGC CCCAAGGCCC AGCCCCAGAC   1800
TTGGAAATCT GGCAAGCAGA CTATGCTGTC TCACTACCGG CCATTCTACG TCAACAAAGG   1860
CAACGGGATT GGGTCCAACG AAGCCCCATG AGCTCCTGGC GGAAGGAACG AGGCGCCACA   1920
CCCCTGCTCT TCCTCCTGAC CCTGCTGCTC TTGCCTTCTA AGCTACTGTG CTTGTCTGGG   1980
TGGGAGGGAG CCTGGTCCTG CACCTGCCCT CTGCAGCCCT CTGCCAGCCT CTTGGGGGCA   2040
GTTCCGGCCT CTCCGACTTC CCCACTGGCC ACACTCCATT CAGACTCCTT TCCTGCCTTG   2100
TGACCTCAGA TGGTCACCAT CATTCCTGTG CTCAGAGGCC AACCCATCAC AGGGGTGAGA   2160
TAGGTTGGGG CCTGCCCTAA CCCGCCAGCC TCCTCCTCTC GGGCTGGATC TGGGGGCTAG   2220
CAGTGAGTAC CCGCATGGTA TCAGCCTGCC TCTCCCGCCC ACGCCCTGCT GTCTCCAGGC   2280
CTATAGACGT TTCTCTCCAA GGCCCTATCC CCAATGTTG TCAGCAGATG CCTGGACAGC   2340
ACAGCCACCC ATCTCCCATT CACATGGCCC ACCTCCTGCT TCCAGAGGA CTGGCCCTAC   2400
GTGCTCTCTC TCGTCCTACC TATCAATGCC CAGCATGGCA GAACCTGCAG TGGCCAAGGG   2460
```

```
CTGCAGATGG  AAACCTCTCA  GTGTCTTGAC  ATCACCCTAC  CCAGGCGGTG  GGTCTCCACC   2520

ACAGCCACTT  TGAGTCTGTG  GTCCCTGGAG  GGTGGCTTCT  CCTGACTGGC  AGGATGACCT   2580

TAGCCAAGAT  ATTCCTCTGT  TCCCTCTGCT  GAGATAAAGA  ATTCCCTTAA  CATGATATAA   2640

TCCACCCATG  CAAATAGCTA  CTGGCCCAGC  TACCATTTAC  CATTTGCCTA  CAGAATTTCA   2700

TTCAGTCTAC  ACTTTGGCAT  TCTCTCTGGC  GATGGAGTGT  GGCTGGGCTG  ACCGCAAAAG   2760

GTGCCTTACA  CACTGCCCCC  ACCCTCAGCC  GTTGCCCCAT  CAGAGGCTGC  CTCCTCCTTC   2820

TGATTACCCC  CCATGTTGCA  TATCAGGGTG  CTCAAGGATT  GGAGAGGAGA  CAAAACCAGG   2880

AGCAGCACAG  TGGGGACATC  TCCCGTCTCA  ACAGCCCCAG  GCCTATGGGG  GCTCTGGAAG   2940

GATGGGCCAG  CTTGCAGGGG  TTGGGGAGGG  AGACATCCAG  CTTGGGCTTT  CCCCTTTGGA   3000

ATAAACCATT  GGTCTGTC                                                    3018
```

( 2 ) INFORMATION FOR SEQ ID NO:2:

( i ) SEQUENCE CHARACTERISTICS:
           ( A ) LENGTH: 1767 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( i x ) FEATURE:
           ( A ) NAME/KEY: CDS
           ( B ) LOCATION: 1..1764

( x i ) SEQUENCE DESCRIPTION: SEQ ID NO:2:

```
ATG  GAA  GCT  GCA  GAT  GCC  TCC  AGG  AGC  AAC  GGG  TCG  AGC  CCA  GAA  GCC        48
Met  Glu  Ala  Ala  Asp  Ala  Ser  Arg  Ser  Asn  Gly  Ser  Ser  Pro  Glu  Ala
 1                    5                        10                       15

AGG  GAT  GCC  CGG  AGC  CCG  TCG  GGC  CCC  AGT  GGC  AGC  CTG  GAG  AAT  GGC        96
Arg  Asp  Ala  Arg  Ser  Pro  Ser  Gly  Pro  Ser  Gly  Ser  Leu  Glu  Asn  Gly
               20                       25                       30

ACC  AAG  GCT  GAC  GGC  AAG  GAT  GCC  AAG  ACC  ACC  AAC  GGG  CAC  GGC  GGG       144
Thr  Lys  Ala  Asp  Gly  Lys  Asp  Ala  Lys  Thr  Thr  Asn  Gly  His  Gly  Gly
          35                       40                       45

GAG  GCA  GCT  GAG  GGC  AAG  AGC  CTG  GGC  AGC  GCC  CTG  AAG  CCA  GGG  GAA       192
Glu  Ala  Ala  Glu  Gly  Lys  Ser  Leu  Gly  Ser  Ala  Leu  Lys  Pro  Gly  Glu
     50                       55                       60

GGT  AGG  AGC  GCC  CTG  TTC  GCG  GGC  AAT  GAG  TGG  CGG  CGA  CCC  ATC  ATC       240
Gly  Arg  Ser  Ala  Leu  Phe  Ala  Gly  Asn  Glu  Trp  Arg  Arg  Pro  Ile  Ile
 65                       70                       75                       80

CAG  TTT  GTC  GAG  TCC  GGG  GAC  GAC  AAG  AAC  TCC  AAC  TAC  TTC  AGC  ATG       288
Gln  Phe  Val  Glu  Ser  Gly  Asp  Asp  Lys  Asn  Ser  Asn  Tyr  Phe  Ser  Met
                         85                       90                       95

GAC  TCT  ATG  GAA  GGC  AAG  AGG  TCG  CCG  TAC  GCA  GGG  CTC  CAG  CTG  GGG       336
Asp  Ser  Met  Glu  Gly  Lys  Arg  Ser  Pro  Tyr  Ala  Gly  Leu  Gln  Leu  Gly
                    100                      105                      110

GCT  GCC  AAG  AAG  CCA  CCC  GTT  ACC  TTT  GCC  GAA  AAG  GGC  GAC  GTG  CGC       384
Ala  Ala  Lys  Lys  Pro  Pro  Val  Thr  Phe  Ala  Glu  Lys  Gly  Asp  Val  Arg
               115                      120                      125

AAG  TCC  ATT  TTC  TCG  GAG  TCC  CGG  AAG  CCC  ACG  GTG  TCC  ATC  ATG  GAG       432
Lys  Ser  Ile  Phe  Ser  Glu  Ser  Arg  Lys  Pro  Thr  Val  Ser  Ile  Met  Glu
          130                      135                      140

CCC  GGG  GAG  ACC  CGG  CGG  AAC  AGC  TAC  CCC  CGG  GCC  GAC  ACG  GGC  CTT       480
Pro  Gly  Glu  Thr  Arg  Arg  Asn  Ser  Tyr  Pro  Arg  Ala  Asp  Thr  Gly  Leu
145                      150                      155                      160

TTT  TCA  CGG  TCC  AAG  TCC  GGC  TCC  GAG  GAG  GTG  CTG  TGC  GAC  TCC  TGC       528
```

| | | | | | | | | | | | | | | | | |
|---|---|---|---|---|---|---|---|---|---|---|---|---|---|---|---|---|
| Phe | Ser | Arg | Ser | Lys 165 | Ser | Gly | Ser | Glu | Glu 170 | Val | Leu | Cys | Asp | Ser 175 | Cys | |
| ATC Ile | GGC Gly | AAC Asn | AAG Lys 180 | CAG Gln | AAG Lys | GCG Ala | GTC Val | AAG Lys 185 | TCC Ser | TGC Cys | CTG Leu | GTG Val | TGC Cys 190 | CAG Gln | GCC Ala | 576 |
| TCC Ser | TTC Phe | TGC Cys 195 | GAG Glu | CTG Leu | CAT His | CTC Leu | AAG Lys 200 | CCC Pro | CAC His | CTG Leu | GAG Glu | GGC Gly 205 | GCC Ala | GCC Ala | TTC Phe | 624 |
| CGA Arg | GAC Asp 210 | CAC His | CAG Gln | CTG Leu | CTC Leu | GAG Glu 215 | CCC Pro | ATC Ile | CGG Arg | GAC Asp | TTT Phe 220 | GAG Glu | GCC Ala | CGC Arg | AAG Lys | 672 |
| TGT Cys 225 | CCC Pro | GTG Val | CAT His | GGC Gly | AAG Lys 230 | ACG Thr | ATG Met | GAG Glu | CTC Leu | TTC Phe 235 | TGC Cys | CAG Gln | ACC Thr | GAC Asp | CAG Gln 240 | 720 |
| ACC Thr | TGC Cys | ATC Ile | TGC Cys | TAC Tyr 245 | CTT Leu | TGC Cys | ATG Met | TTC Phe | CAG Gln 250 | GAG Glu | CAC His | AAG Lys | AAT Asn | CAT His 255 | AGC Ser | 768 |
| ACC Thr | GTG Val | ACA Thr | GTG Val | GAG Glu 260 | GAG Glu | GCC Ala | AAG Lys | GCC Ala | GAG Glu 265 | AAG Lys | GAG Glu | ACG Thr | GAG Glu 270 | CTG Leu | TCA Ser | 816 |
| CTG Leu | CAA Gln | AAG Lys 275 | GAG Glu | CAG Gln | CTG Leu | CAG Gln | CTC Leu 280 | AAG Lys | ATC Ile | ATT Ile | GAG Glu | ATT Ile 285 | GAG Glu | GAT Asp | GAA Glu | 864 |
| GCT Ala | GAG Glu | AAG Lys 290 | TGG Trp | CAG Gln | AAG Lys | GAG Glu | AAG Lys 295 | GAC Asp | CGC Arg | ATC Ile | AAG Lys | AGC Ser 300 | TTC Phe | ACC Thr | ACC Thr | 912 |
| AAT Asn 305 | GAG Glu | AAG Lys | GCC Ala | ATC Ile | CTG Leu 310 | GAG Glu | CAG Gln | AAC Asn | TTC Phe | CGG Arg 315 | GAC Asp | CTG Leu | GTG Val | CGG Arg | GAC Asp 320 | 960 |
| CTG Leu | GAG Glu | AAG Lys | CAA Gln | AAG Lys 325 | GAG Glu | GAA Glu | GTG Val | AGG Arg | GCT Ala 330 | GCG Ala | CTG Leu | GAG Glu | CAG Gln | CGG Arg 335 | GAG Glu | 1008 |
| CAG Gln | GAT Asp | GCT Ala | GTG Val 340 | GAC Asp | CAA Gln | GTG Val | AAG Lys | GTG Val 345 | ATC Ile | ATG Met | GAT Asp | GCT Ala | CTG Leu 350 | GAT Asp | GAG Glu | 1056 |
| AGA Arg | GCC Ala | AAG Lys 355 | GTG Val | CTG Leu | CAT His | GAG Glu | GAC Asp 360 | AAG Lys | CAG Gln | ACC Thr | CGG Arg | GAG Glu 365 | CAG Gln | CTG Leu | CAT His | 1104 |
| AGC Ser | ATC Ile | AGC Ser 370 | GAC Asp | TCT Ser | GTG Val | TTG Leu | TTT Phe 375 | CTG Leu | CAG Gln | GAA Glu | TTT Phe | GGT Gly 380 | GCA Ala | TTG Leu | ATG Met | 1152 |
| AGC Ser 385 | AAT Asn | TAC Tyr | TCT Ser | CTC Leu | CCC Pro 390 | CCA Pro | CCC Pro | CTG Leu | CCC Pro | ACC Thr 395 | TAT Tyr | CAT His | GTC Val | CTG Leu | CTG Leu 400 | 1200 |
| GAG Glu | GGG Gly | GAG Glu | GGC Gly | CTG Leu 405 | GGA Gly | CAG Gln | TCA Ser | CTA Leu | GGC Gly 410 | AAC Asn | TTC Phe | AAG Lys | GAC Asp | CTG Leu 415 | CTG Leu | 1248 |
| CTC Leu | AAT Asn | GTA Val | TGC Cys 420 | ATG Met | CGC Arg | CAC His | GTT Val | GAG Glu 425 | AAG Lys | ATG Met | TGC Cys | AAG Lys | GCG Ala 430 | GAC Asp | CTG Leu | 1296 |
| AGC Ser | CGT Arg | AAC Asn 435 | TTC Phe | ATT Ile | GAG Glu | AGG Arg | AAC Asn 440 | CAC His | ATG Met | GAG Glu | AAC Asn | GGT Gly 445 | GGT Gly | GAC Asp | CAT His | 1344 |
| CGC Arg | TAT Tyr 450 | GTG Val | AAC Asn | AAC Asn | TAC Tyr | ACG Thr 455 | AAC Asn | AGC Ser | TTC Phe | GGG Gly | GGT Gly 460 | GAG Glu | TGG Trp | AGT Ser | GCA Ala | 1392 |
| CCG Pro 465 | GAC Asp | ACC Thr | ATG Met | AAG Lys | AGA Arg 470 | TAC Tyr | TCC Ser | ATG Met | TAC Tyr | CTG Leu 475 | ACA Thr | CCC Pro | AAA Lys | GGT Gly | GGG Gly 480 | 1440 |
| GTC Val | CGG Arg | ACA Thr | TCA Ser | TAC Tyr 485 | CAG Gln | CCC Pro | TCG Ser | TCT Ser | CCT Pro 490 | GGC Gly | CGC Arg | TTC Phe | ACC Thr | AAG Lys 495 | GAG Glu | 1488 |

| | | | | | | | | | | | | | | | |
|---|---|---|---|---|---|---|---|---|---|---|---|---|---|---|---|
| ACC | ACC | CAG | AAG | AAT | TTC | AAC | AAT | CTC | TAT | GGC | ACC | AAA | GGT | AAC | TAC | 1536
| Thr | Thr | Gln | Lys | Asn | Phe | Asn | Asn | Leu | Tyr | Gly | Thr | Lys | Gly | Asn | Tyr |
| | | | 500 | | | | | 505 | | | | | 510 | | |
| ACC | TCC | CGG | GTC | TGG | GAG | TAC | TCC | TCC | AGC | ATT | CAG | AAC | TCT | GAC | AAT | 1584
| Thr | Ser | Arg | Val | Trp | Glu | Tyr | Ser | Ser | Ser | Ile | Gln | Asn | Ser | Asp | Asn |
| | | 515 | | | | | 520 | | | | | 525 | | | |
| GAC | CTG | CCC | GTC | GTC | CAA | GGC | AGC | TCC | TCC | TTC | TCC | CTG | AAA | GGC | TAT | 1632
| Asp | Leu | Pro | Val | Val | Gln | Gly | Ser | Ser | Ser | Phe | Ser | Leu | Lys | Gly | Tyr |
| | 530 | | | | | 535 | | | | | 540 | | | | |
| CCC | TCC | CTC | ATG | CGG | AGC | CAA | AGC | CCC | AAG | GCC | CAG | CCC | CAG | ACT | TGG | 1680
| Pro | Ser | Leu | Met | Arg | Ser | Gln | Ser | Pro | Lys | Ala | Gln | Pro | Gln | Thr | Trp |
| 545 | | | | | 550 | | | | | 555 | | | | | 560 |
| AAA | TCT | GGC | AAG | CAG | ACT | ATG | CTG | TCT | CAC | TAC | CGG | CCA | TTC | TAC | GTC | 1728
| Lys | Ser | Gly | Lys | Gln | Thr | Met | Leu | Ser | His | Tyr | Arg | Pro | Phe | Tyr | Val |
| | | | | 565 | | | | | 570 | | | | | 575 | |
| AAC | AAA | GGC | AAC | GGG | ATT | GGG | TCC | AAC | GAA | GCC | CCA | TGA | | | | 1767
| Asn | Lys | Gly | Asn | Gly | Ile | Gly | Ser | Asn | Glu | Ala | Pro | | | | |
| | | | 580 | | | | | 585 | | | | | | | |

( 2 ) INFORMATION FOR SEQ ID NO:3:

( i ) SEQUENCE CHARACTERISTICS:
        ( A ) LENGTH: 588 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:3:

| | | | | | | | | | | | | | | |
|---|---|---|---|---|---|---|---|---|---|---|---|---|---|---|
| Met | Glu | Ala | Ala | Asp | Ala | Ser | Arg | Ser | Asn | Gly | Ser | Ser | Pro | Glu | Ala |
| 1 | | | | 5 | | | | | 10 | | | | | 15 | |
| Arg | Asp | Ala | Arg | Ser | Pro | Ser | Gly | Pro | Ser | Gly | Ser | Leu | Glu | Asn | Gly |
| | | | 20 | | | | | 25 | | | | | 30 | | |
| Thr | Lys | Ala | Asp | Gly | Lys | Asp | Ala | Lys | Thr | Thr | Asn | Gly | His | Gly | Gly |
| | | | 35 | | | | 40 | | | | | 45 | | | |
| Glu | Ala | Ala | Glu | Gly | Lys | Ser | Leu | Gly | Ser | Ala | Leu | Lys | Pro | Gly | Glu |
| | 50 | | | | | 55 | | | | | 60 | | | | |
| Gly | Arg | Ser | Ala | Leu | Phe | Ala | Gly | Asn | Glu | Trp | Arg | Arg | Pro | Ile | Ile |
| 65 | | | | | 70 | | | | | 75 | | | | | 80 |
| Gln | Phe | Val | Glu | Ser | Gly | Asp | Asp | Lys | Asn | Ser | Asn | Tyr | Phe | Ser | Met |
| | | | | 85 | | | | | 90 | | | | | 95 | |
| Asp | Ser | Met | Glu | Gly | Lys | Arg | Ser | Pro | Tyr | Ala | Gly | Leu | Gln | Leu | Gly |
| | | | 100 | | | | | 105 | | | | | 110 | | |
| Ala | Ala | Lys | Lys | Pro | Pro | Val | Thr | Phe | Ala | Glu | Lys | Gly | Asp | Val | Arg |
| | | | 115 | | | | 120 | | | | | 125 | | | |
| Lys | Ser | Ile | Phe | Ser | Glu | Ser | Arg | Lys | Pro | Thr | Val | Ser | Ile | Met | Glu |
| | | 130 | | | | 135 | | | | | 140 | | | | |
| Pro | Gly | Glu | Thr | Arg | Arg | Asn | Ser | Tyr | Pro | Arg | Ala | Asp | Thr | Gly | Leu |
| | 145 | | | | | 150 | | | | | 155 | | | | 160 |
| Phe | Ser | Arg | Ser | Lys | Ser | Gly | Ser | Glu | Glu | Val | Leu | Cys | Asp | Ser | Cys |
| | | | | 165 | | | | | 170 | | | | | 175 | |
| Ile | Gly | Asn | Lys | Gln | Lys | Ala | Val | Lys | Ser | Cys | Leu | Val | Cys | Gln | Ala |
| | | | 180 | | | | 185 | | | | | 190 | | | |
| Ser | Phe | Cys | Glu | Leu | His | Leu | Lys | Pro | His | Leu | Glu | Gly | Ala | Ala | Phe |
| | | 195 | | | | 200 | | | | | 205 | | | | |
| Arg | Asp | His | Gln | Leu | Leu | Glu | Pro | Ile | Arg | Asp | Phe | Glu | Ala | Arg | Lys |
| | | 210 | | | | 215 | | | | | 220 | | | | |
| Cys | Pro | Val | His | Gly | Lys | Thr | Met | Glu | Leu | Phe | Cys | Gln | Thr | Asp | Gln |

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |

Thr Cys Ile Cys Tyr Leu Cys Met Phe Gln Glu His Lys Asn His Ser
            245                     250                 255

Thr Val Thr Val Glu Glu Ala Lys Ala Glu Lys Glu Thr Glu Leu Ser
            260             265             270

Leu Gln Lys Glu Gln Leu Gln Leu Lys Ile Ile Glu Ile Glu Asp Glu
        275             280             285

Ala Glu Lys Trp Gln Lys Glu Lys Asp Arg Ile Lys Ser Phe Thr Thr
    290             295             300

Asn Glu Lys Ala Ile Leu Glu Gln Asn Phe Arg Asp Leu Val Arg Asp
305             310             315             320

Leu Glu Lys Gln Lys Glu Glu Val Arg Ala Ala Leu Glu Gln Arg Glu
                325             330             335

Gln Asp Ala Val Asp Gln Val Lys Val Ile Met Asp Ala Leu Asp Glu
            340             345             350

Arg Ala Lys Val Leu His Glu Asp Lys Gln Thr Arg Glu Gln Leu His
        355             360             365

Ser Ile Ser Asp Ser Val Leu Phe Leu Gln Glu Phe Gly Ala Leu Met
    370             375             380

Ser Asn Tyr Ser Leu Pro Pro Leu Pro Thr Tyr His Val Leu Leu
385             390             395             400

Glu Gly Glu Gly Leu Gly Gln Ser Leu Gly Asn Phe Lys Asp Asp Leu
            405             410             415

Leu Asn Val Cys Met Arg His Val Glu Lys Met Cys Lys Ala Asp Leu
            420             425             430

Ser Arg Asn Phe Ile Glu Arg Asn His Met Glu Asn Gly Gly Asp His
        435             440             445

Arg Tyr Val Asn Asn Tyr Thr Asn Ser Phe Gly Gly Glu Trp Ser Ala
    450             455             460

Pro Asp Thr Met Lys Arg Tyr Ser Met Tyr Leu Thr Pro Lys Gly Gly
465             470             475             480

Val Arg Thr Ser Tyr Gln Pro Ser Ser Pro Gly Arg Phe Thr Lys Glu
            485             490             495

Thr Thr Gln Lys Asn Phe Asn Asn Leu Tyr Gly Thr Lys Gly Asn Tyr
        500             505             510

Thr Ser Arg Val Trp Glu Tyr Ser Ser Ser Ile Gln Asn Ser Asp Asn
    515             520             525

Asp Leu Pro Val Val Gln Gly Ser Ser Ser Phe Ser Leu Lys Gly Tyr
530             535             540

Pro Ser Leu Met Arg Ser Gln Ser Pro Lys Ala Gln Pro Gln Thr Trp
545             550             555             560

Lys Ser Gly Lys Gln Thr Met Leu Ser His Tyr Arg Pro Phe Tyr Val
            565             570             575

Asn Lys Gly Asn Gly Ile Gly Ser Asn Glu Ala Pro
            580             585

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:4:

TCTCTAGTCC TCGTGGTT  18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:5:

GGTGGTCTTG GCATCCTT  18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:6:

TGGAGAATGG CACCAAGG  18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:7:

TCCATGATGG ACACCGTG  18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:8:

TCTATGGAAG GCAAGAGG  18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:9:

GGAGAAGATG AAGTTCGG        18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:10:

TGACTTCTCC AATCCTGG        18

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:11:

CCTGGACTCA AATGGGAG        18

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:12:

AAGACATACC CGACTAGG        18

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:13:

TGTGAAATCG AGGGCTTG 18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:14:

AGCGTCCTCA TAGCTCAT 18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:15:

TGAGAAGAAG CTCACTGG 18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:16:

AAACTTGGAT CTGCCTGG 18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO ( i v ) ANTI-SENSE: NO ( x i ) SEQUENCE DESCRIPTION: SEQ ID NO:17:

AGTCACTGCA CGGACTTT                                                                                          18

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:18:

GAGTCCTGAT GAGACAAT                                                                                          18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:19:

CATTCATCTC ACACTGGG                                                                                          18

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:20:

AGAGAGTCAT AGACCTGG                                                                                          18

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:21:

GAGCAACTAG CAGCTCAG                                                                                          18

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:22:

GACGGCTGCA TTTGGTAA    18

( 2 ) INFORMATION FOR SEQ ID NO:23:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:23:

CAGAGAAGTC CTCCCACA    18

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:24:

AGAATTGTCG GGTCTTGG    18

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: PCR primer ( i i i ) HYPOTHETICAL: NO ( i v ) ANTI-SENSE: NO ( x i ) SEQUENCE DESCRIPTION: SEQ ID NO:25:

GCACAGTAGC TTAGAAGG    18

( 2 ) INFORMATION FOR SEQ ID NO:26:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:26:

ACAAAGGCAA CGGGATTG    18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:27:

TCTGCTGACA ACATTGGG    18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:28:

AGACGTTTCT CTCCAAGG    18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (iv) ANTI-SENSE: NO (xi) SEQUENCE DESCRIPTION: SEQ ID NO:29:

CTTTATCTCA GCAGAGGG    18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: PCR primer (iii) HYPOTHETICAL: NO (i v) ANTI-SENSE: NO (x i) SEQUENCE DESCRIPTION: SEQ ID NO:30:

AGGATGACCT TAGCCAAG    18

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: PCR primer (i i i) HYPOTHETICAL: NO (i v) ANTI-SENSE: NO (x i) SEQUENCE DESCRIPTION: SEQ ID NO:31:

GAAGAACTGC AGCCTGTT    18

(2) INFORMATION FOR SEQ ID NO:32:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:32:

```
TCTCTAGTCC TCGTGGTTGC CTGCCCCACT CCCTGCCGAG ACGCCTGCCA GAAAGGTCAC    60
CTATCCTGAA CCCCAGCAAG CCTGAAACAG CTCAGCCAAG CACCCTGCGA TGGAAGCTGC   120
AGATGCCTCC AGGAGCAACG GGTCGAGCCC AGAAGCCAGG GATGCCCGGA GCCCGTCGGG   180
CCCCAGTGGC AGCCTGGAGA ATGGCACCAA GGCTGACGGC AAGGATGCCA AGACCACC    238
```

(2) INFORMATION FOR SEQ ID NO:33:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:33:

```
TGGAGAATGG CACCAAGGCT GACGGCAAGG ATGCCAAGAC CACCAACGGG CACGGCGGGG    60
AGGCAGCTGA GGGCAAGAGC CTGGGCAGCG CCCTGAAGCC AGGGGAAGGT AGGAGCGCCC   120
TGTTCGCGGG CAATGAGTGG CGGCGACCCA TCATCCAGTT TGTCGAGTCC GGGGACGACA   180
AGAACTCCAA CTACTTCAGC ATGGACTCTA TGGAAGGCAA GAGGTCGCCG TACGCAGGGC   240
TCCAGCTGGG GGCTGCCAAG AAGCCACCCG TTACCTTTGC CGAAAAGGGC GACGTGCGCA   300
AGTCCATTTT CTCGGAGTCC CGGAAGCCCA CGGTGTCCAT CATGGA   346
```

(2) INFORMATION FOR SEQ ID NO:34:

( i ) SEQUENCE CHARACTERISTICS:
  ( A ) LENGTH: 587 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

| | | | | | | |
|---|---|---|---|---|---|---|
| TCTATGGAAG | GCAAGAGGTC | GCCGTACGCA | GGGCTCCAGC | TGGGGGCTGC | CAAGAAGCCA | 60 |
| CCCGTTACCT | TTGCCGAAAA | GGGCGACGTG | CGCAAGTCCA | TTTTCTCGGA | GTCCCGGAAG | 120 |
| CCCACGGTGT | CCATCATGGA | GCCCGGGGAG | ACCCGGCGGA | ACAGCTACCC | CCGGGCCGAC | 180 |
| ACGGGCCTTT | TTTCACGGTC | CAAGTCCGGC | TCCGAGGAGG | TGCTGTGCGA | CTCCTGCATC | 240 |
| GGCAACAAGC | AGAAGGCGGT | CAAGTCCTGC | CTGGTGTGCC | AGGCCTCCTT | CTGCGAGCTG | 300 |
| CATCTCAAGC | CCCACCTGGA | GGGCGCCGCC | TTCCGAGACC | ACCAGCTGCT | CGAGCCCATC | 360 |
| CGGGACTTTG | AGGCCCGCAA | GTGTCCCGTG | CATGGCAAGA | CGATGGAGCT | CTTCTGCCAG | 420 |
| ACCGACCAGA | CCTGCATCTG | CTACCTTTGC | ATGTTCCAGG | AGCACAAGAA | TCATAGCACC | 480 |
| GTGACAGTGG | AGGAGGCCAA | GGCCGAGAAG | GAGGTAAGTG | CTGGGGCCCC | TCCTGCCCCT | 540 |
| CCAGGCCTCT | CCTCTCTCAA | CCCACCCCTC | CGAACTTCAT | CTTCTCC | | 587 |

( 2 ) INFORMATION FOR SEQ ID NO:35:

( i ) SEQUENCE CHARACTERISTICS:
  ( A ) LENGTH: 218 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:35:

| | | | | | | |
|---|---|---|---|---|---|---|
| TGACTTCTCC | AATCCTGGCT | CTTTCTCTGC | AGACGGAGCT | GTCACTGCAA | AAGGAGCAGC | 60 |
| TGCAGCTCAA | GATCATTGAG | ATTGAGGATG | AAGCTGAGAA | GTGGCAGAAG | GAGAAGGACC | 120 |
| GCATCAAGGT | GAGCAGCCCC | CAAGCTCACC | TTGCTGCTCC | CTTACCCGAC | CTGGCCTGCC | 180 |
| TGGAAAGACG | CAGGCCTTGG | CTCCCATTTG | AGTCCAGG | | | 218 |

( 2 ) INFORMATION FOR SEQ ID NO:36:

( i ) SEQUENCE CHARACTERISTICS:
  ( A ) LENGTH: 353 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:36:

| | | | | | | |
|---|---|---|---|---|---|---|
| AAGACATACC | CGACTAGGGT | GATTTCTTTC | CCTAACTAAA | GCCCTGCCTA | ATCTCTTCCC | 60 |
| TGACTCTGGA | CCTCCAGAGC | TTCACCACCA | ATGAGAAGGC | CATCCTGGAG | CAGAACTTCC | 120 |
| GGGACCTGGT | GCGGGACCTG | GAGAAGCAAA | AGGAGGAAGT | GAGGGCTGCG | CTGGAGCAGC | 180 |

| GGGAGCAGGA | TGCTGTGGAC | CAAGTGAAGG | TGATCATGGA | TGCTCTGGAT | GAGAGAGCCA | 240 |
| AGGTGCTGCA | TGAGGACAAG | CAGACCCGGG | AGCAGCTGCA | TAGCATCAGC | GACTCTGTGT | 300 |
| TGTTTCTGCA | GGTAACAAGC | CACTCCTCTG | TCACTCAAGC | CCTCGATTTC | ACA | 353 |

( 2 ) INFORMATION FOR SEQ ID NO:37:

( i ) SEQUENCE CHARACTERISTICS:
        ( A ) LENGTH: 359 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:37:

| AGCGTCCTCA | TAGCTCATGA | AGACCCAGGC | AGTTAATGGT | TCTTTCCTTT | CTTGGTAGGA | 60 |
| ATTTGGTGCA | TTGATGAGCA | ATTACTCTCT | CCCCCCACCC | CTGCCCACCT | ATCATGTCCT | 120 |
| GCTGGAGGGG | GAGGGCCTGG | GACAGTCACT | AGGCAACTTC | AAGGACGACC | TGCTCAATGT | 180 |
| ATGCATGCGC | CACGTTGAGA | AGATGTGCAA | GGCGGACCTG | AGCCGTAACT | TCATTGAGAG | 240 |
| GAACCACATG | GAGAACGGTA | GGTCCCCTCT | CGTGGCTGGG | CCCCAAGGCC | ATAGACCTTT | 300 |
| CTCTCCCAAA | TCAATTCCTG | CTGCCTGACA | TGGGCTGGCC | TCCAGTGAGC | TTCTTCTCA | 359 |

( 2 ) INFORMATION FOR SEQ ID NO:38:

( i ) SEQUENCE CHARACTERISTICS:
        ( A ) LENGTH: 304 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:38:

| AAACTTGGAT | CTGCCTGGGA | GATAGGGGAA | GGGCTATGGG | GTGACTCATC | TGAGCCCCAA | 60 |
| AAGTCCCCAG | TGGCTGGCTC | CTCCTTCCCA | CCTGGCTCCT | CTGCTGACCC | GACCCTCTGC | 120 |
| TTCCTAGGTG | GTGACCATCG | CTATGTGAAC | AACTACACGA | ACAGCTTCGG | GGGTGAGTGG | 180 |
| AGTGCACCGG | ACACCATGAA | GAGATACTCC | ATGTACCTGA | CACCCAAAGG | TAAGAGGGAG | 240 |
| CCCCTCACCC | CAGACCTAGT | GTCTCTCCTG | CTGCCCAGGG | GCCCCAAAG | TCCGTGCAGT | 300 |
| GACT | | | | | | 304 |

( 2 ) INFORMATION FOR SEQ ID NO:39:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:39:

```
GAGTCCTGAT GAGACAATTT TGTGCAATGA CAGCCCNNTT CATCTGCTTC ACAGGTGGGG        60

TCCGGACATC ATACCAGCCC TCGTCTCCTG GCCGCTTCAC CAAGGAGACC ACCCAGAAGA       120

ATTTCAACAA TCTCTATGGC ACCAAGNNN NNNNTGGGNC TGTGCAGGCA GGAGGGCATA       180

GAGGTGGGTC CAGNGGCACA GGGCTGGGAC CCCAGTGTGA GATGAATG                    228
```

( 2 ) INFORMATION FOR SEQ ID NO:40:

( i ) SEQUENCE CHARACTERISTICS:
        ( A ) LENGTH: 283 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:40:

```
AGAGAGTCAT AGACCTGGCT GTGTCCTGGT CCTGCCTCCT CTCCCACTCC CAGCTGTGGG        60

GGCCTGACAG CCCTTCTTTG TCCTGNAAGG TAACTACACC TCCCGGGTCT GGGAGTACTC       120

CTCCAGCATT CAGAACTCTG ACAATGACCT GCCCGTCGTC CAAGGCAGCT CCTCCTTCTC       180

CCTGAAAGGT GAGCCCTGCC CACCCTGGCC CCTGCTTTCC TCCACAGCTG CCTCACACCT       240

CCCAAGCCCT GCTTGGGTCT CTTCGCTGAG CTGCTAGTTC CTC                         283
```

( 2 ) INFORMATION FOR SEQ ID NO:41:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:41:

```
GACGGCTGCA TTTGGTAATG GGCTGGATGA TGCTTGGTGG TACACTTTGG AGAAGNAGCT        60

GTGCTGCTCT GGGNCCGGGN NCCCCTGGCC NNNNNNNNNN NNNNNNNNNN NNNNNNNNNN       120

NNNNNNNNNN NNGCTATCCC TCCCTCATGC GGAGCCAAAG CCCCAAGGCC CAGCCCCAGA       180

CTTGGAAATC TGGCAAGCAG ACTATGCTGG TAAGGGAAGT GCTGCCGGGA GGGCCTGGGC       240

ACATCCAGAG ACCTGGGCAC TGAAGGGGGC TCCCTGGAGG CAATCGGTTC CAGGGCCTGT       300

GGGAGGACTT CTCTG                                                         315
```

( 2 ) INFORMATION FOR SEQ ID NO:42:

( i ) SEQUENCE CHARACTERISTICS:
        ( A ) LENGTH: 259 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:42:

```
AGAATTGTCG GGTCTTGGAT CACTGCTGCC TCCTGAGGCA GGTTAGGGTA GGGTGGGTCT        60
```

5,395,767

-continued

```
AGCTAGCAGG CTCATCTGTC GTCTGGCCTC GCTGACCACT CTTGTTTCCC CCACAGTCTC    120

ACTACCGGCC ATTCTACGTC AACAAAGGCA ACGGGATTGG GTCCAACGAA GCCCCATGAG    180

CTCCTGGCGG AAGGAACGAG GCGCCACACC CCTGCTCTTC CTCCTGACCC TGCTGCTCTT    240

GCCTTCTAAG CTACTGTGC                                                 259
```

( 2 ) INFORMATION FOR SEQ ID NO:43:

( i ) SEQUENCE CHARACTERISTICS:
        ( A ) LENGTH: 475 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:43:

```
ACAAAGGCAA CGGGATTGGG TCCAACGAAG CCCCATGAGC TCCTGGCGGA AGGAACGAGG     60

CGCCACACCC CTGCTCTTCC TCCTGACCCT GCTGCTCTTG CCTTCTAAGC TACTGTGCTT    120

GYCTGGGTGG GAGGGAGCCT GGTCCTGCAC CTGCCCTCTG CAGCCCTCTG CCAGCCTCTT    180

GGGGGCAGTT CCGGCCTCTC CGACTTCCCC ACTGGCCACA CTCCATTCAG ACTCCTTTCC    240

TGCCTTGTGA CCTCAGATGG TCACCATCAT TCCTGTGCTC AGAGGCCAAC CCATCACAGG    300

GGTGAGATAG GTTGGGGCCT GCCCTAACCC GCCAGCCTCC TCCTCTCGGG CTGGATCTGG    360

GGGCTAGCAG TGAGTACCCG CATGGTATCA GCCTGCCTCT CCCGCCCACG CCCTGCTGTC    420

TCCAGGCCTA TAGACGTTTC TCTCCAAGGC CCTATCCCCC AATGTTGTCA GCAGA         475
```

( 2 ) INFORMATION FOR SEQ ID NO:44:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:44:

```
AGACGTTTCT CTCCAAGGCC CTATCCCCCA ATGTTGTCAG CAGATGCCTG GACAGCACAG     60

CCACCCATCT CCCATTCACA TGGCCCACCT CCTGCTTCCC AGAGGACTGG CCCTACGTGC    120

TCTCTCTCGT CCTACCTATC AATGCCCAGC ATGGCAGAAC CTGCAGTGGC CAAGGGCTGC    180

AGATGGAAAC CTCTCAGTGT CTTGACATCA CCCTACCCAG GCGGTGGGTC TCCACCACAG    240

CCACTTTGAG TCTGTGGTCC CTGGAGGGTG GCTTCTCCTG ACTGGCAGGA TGACCTTAGC    300

CAAGATATTC CTCTGTTCCC TCTGCTGAGA TAAAG                               335
```

( 2 ) INFORMATION FOR SEQ ID NO:45:

( i ) SEQUENCE CHARACTERISTICS:
        ( A ) LENGTH: 511 base pairs
        ( B ) TYPE: nucleic acid
        ( C ) STRANDEDNESS: single
        ( D ) TOPOLOGY: linear ( i i ) MOLECULE TYPE: DNA (genomic)

(  i i i  ) HYPOTHETICAL: NO (  i v  ) ANTI-SENSE: NO (  x i  ) SEQUENCE DESCRIPTION: SEQ ID NO:45:

| | | | | | |
|---|---|---|---|---|---|
| AGGATGACCT | TAGCCAAGAT | ATTCCTCTGT | TCCCTCTGCT | GAGATAAAGA | ATTCCCTTAA | 60
| CATGATATAA | TCCACCCATG | CAAATAGCTA | CTGGCCCAGC | TACCATTTAC | CATTTGCCTA | 120
| CAGAATTTCA | TTCAGTCTAC | ACTTTGGCAT | TCTCTCTGGC | GATGGAGTGT | GGCTGGGCTG | 180
| ACCGCAAAAG | GTGCCTTACA | CACTGCCCCC | ACCCTCAGCC | GTTGCCCCAT | CAGAGGCTGC | 240
| CTCCTCCTTC | TGATTACCCC | CCATGTTGCA | TATCAGGGTG | CTCAAGGATT | GGAGAGGAGA | 300
| CAAAACCAGG | AGCAGCACAG | TGGGGACATC | TCCCGTCTCA | ACAGCCCCAG | GCCTATGGGG | 360
| GCTCTGGAAG | GATGGGCCAG | CTTGCAGGGG | TTGGGGAGGG | AGACATCCAG | CTTGGGCTTT | 420
| CCCCTTTGGA | ATAAACCATT | GGTCTGTCAC | TTCTCTTGTA | TTGAATGACC | ATTTCCCTGA | 480
| GGGTCCCCAG | AGGAACAGGC | TGCAGTTCTT | C | | | 511

GENE FOR ATAXIA-TELANGIECTASIA COMPLEMENTATION GROUP D (ATDC)

This invention was made with Government support under Contract Nos. DE-AC03-76-SF01012 and W-7405-ENG-48, awarded by the Department of Energy. The Government has certain rights in this invention.

FIELD OF THE INVENTION

The present invention is in the general area of medical genetics. More specifically, it relates to the identification of a new gene—the ataxia-telangiectasia group D gene—the ATDC gene.

BACKGROUND OF THE INVENTION

Ataxia-telangiectasia (AT) is a human autosomal recessive disease that exhibits progressive neuromuscular problems, immunodeficiencies, a high incidence of lymphoreticular cancer, and sensitivity to ionizing radiation [Taylor, "Cytogenetics of ataxia telangiectasia, IN: Bridges and Harnden (eds.) *Ataxia-telangiectasia—a cellular and molecular link between cancer, neuropathology and immune deficiency*, pp. 53–82 (Wiley, Chichester 1988); Boder, "Ataxia telangiectasia an overview," IN: Gatti and Swift (eds.), *Ataxia telangiectasia: genetics, neuropathology and immunology of a degenerative disease of childhood*, pp. 1–63 (Alan R. Liss; New York, 1985); and Morrell et al., *J. Natl. Cancer Inst.*, 77: 89–92 (1986)]. AT heterozygotes, which constitute as much as 3% of the human population, have been reported to have an increased risk of cancer after exposure to ionizing radiation.

Cells from patients with AT display two hallmark characteristics: hypersensitivity to the killing effects of ionizing radiation [Taylor et al., *Nature*, 258: 427–429 (1975)] and resistance to the inhibiting effects of ionizing radiation on the rate of DNA synthesis, that is, radioresistant DNA synthesis [Young and Painter, *Hum. Genet.*, 82: 113–117 (1989)]. Thus, the identification of genes that are responsible for those abnormalities would greatly further the understanding of human radiosensitivity and the regulation of DNA replication after radiation-induced DNA damage. The characteristic of AT cells to exhibit radioresistant DNA synthesis has been used to establish the presence of several complementation groups within this disease [Jaspers and Bootsma, *PNAS* (USA), 79: 2641–2644 (1982); Murnane and Painter, *PNAS* (USA), 79: 1960–1963 (1982); Jaspers et al., *Cytogenet. Cell Genet.*, 49: 259–263 (1988)].

Despite extensive investigation, the underlying defects responsible for the pleiotropic abnormalities presented by AT remain unknown. Genetic linkage analysis [Gatti et al., *Nature*, 336: 577–580 (1988); McConville et al., *Nucl. Acids Res.*, 18: 4335–4343 (1990a); McConville et al., *Hum. Genet.*, 85: 215–220 (1990b); Sanal et al., *Am. J. Hum. Genet.*, 47.: 860–866 (1990); and Ziv et al., *Genomics*, 9:373–375 (1991)] and chromosome transfer studies [Lambert et al., *PNAS* (USA), 88: 5907–5911 (1991)] have shown that the gene(s) associated with three complementation groups are all located at the chromosomal region 11q22-q23.

Complementation groups A (AT-A) and C (AT-C) have been mapped by genetic linkage analysis [Gatti et al. 1988; McConville et al. 1990a and 1990b; Sanal et al. 1990; Ziv et al. 1991; and Foroud et al., *Am. J. Hum. Genet.*, 49: 1263–1279 (1991)]. Using families from mixed complementation groups, two groups of investigators independently reported linkage of the AT gene(s) to two separate regions, one of which is near THY1 [McConville et al. 1990a and 1990b; Sanal et al. 1990; Foroud et al. 1991]. It was subsequently determined that the genes for AT-A and AT-C are located within the more centromeric of these two regions [McConville et al. 1990a; Sanal et al. 1990; Foroud et al. 1991], although it was concluded that the AT gene in a small subset of families could map to the second locus near THY1 [Sanal et al. 1990]. A recent study by Gatti et al. [in paper entitled "Ataxia-telangiectasia: linking evidence for genetic heterogeneity," presented at AACR (American Association for Cancer Research) Special Conference "Cellular Responses to Environmental DNA Damage" in Banff, Alberta (Canada) Dec. 1–6, 1991] which excluded families in complementation groups A and C, concluded that a gene for an additional complementation group does show linkage to the region near THY1. The gene for complementation group D (AT-D) was a likely candidate for linkage near THY1 as complementation group D is the next most common complementation group for AT after A and C [Jaspers et al. 1988].

Functional complementation has been used to prove the identity of several genes that provide resistance to various DNA-damaging agents [van Duin et al., *Cell*, 44: 913–923 (1986); Thompson et al., *Mol. Cell Biol.*, 10: 6160–6171 (1990); and Weeda et al., *Mol. Cell Biol.*, 10: 2570–2581 (1990)].

Using the sensitivity of AT cells to ionizing radiation, Kapp and Painter [*Int. J. Radiat. Biol.*, 56: 667–675 (1989)] attempted to complement the defect in an AT cell line (AT5BIVA) from complementation group D (AT-D) by transfection with a human cosmid library containing a selectable neo gene. The combined selection by ionizing radiation and G418 resulted in the isolation of an AT cell line (1B3) that is partially resistant (approximately 50% of normal) to ionizing radiation and produces fewer radiation-induced chromosome aberrations, but retains the AT characteristic of radioresistant DNA synthesis. Southern blot analysis demonstrated that the 1B3 cell line contains at least three cosmids that appear to be integrated in tandem and coamplified [Kapp and Painter 1989, id.]. Transfer of cellular DNA containing those integrated cosmid sequences to AT5BIVA cells produced cell clones with radioresistance similar to that of 1B3 cells, indicating that a gene within the cosmids complements the defect in the AT-D group [Kapp and Painter 1989, id].

Functional complementation of that same cell line (AT5BIVA) has been accomplished by microcell-mediated chromosome transfer from mouse-human hybrids [Lambert et al. 1991]. That study showed that the gene for AT-D was within a recombinant chromosome that contained a human chromosome 11q23 fragment that was telomeric to the AT-A and AT-C linkage region. However, the report did not state whether that mouse-human hybrid also contained the chromosome 11q23 region telomeric to THY1.

The inventors hereof cloned DNA from a fragment of an AT gene for complementation group D. That DNA was of value as a probe to find and clone an entire AT gene for complementation group D, that is, an ATDC gene, and to identify a region in 11q23 where the ATDC gene is located. Prior to the cloning described herein, basic research and clinical work on AT had moved very slowly as there had been no specific gene recognized for AT. Further, there had been no simple biochemical or laboratory test to identify AT patients and/or AT heterozygotes accurately or to classify patients into various complementation groups. The instant invention provides a clear direction for AT research and the means to identify mutations in ATDC genes. Identifying such mutations provides for methods to diagnose AT, preferably AT-D, and to detect AT heterozygotes, preferably AT-D heterozygotes. Detection of AT heterozygotes is important because they have been reported to have an increased risk of cancer in response to treatment with ionizing radiation [Swift et al., *N. Engl. J. Med.*, 325: 1831-1836 (1991)].

SUMMARY OF THE INVENTION

Herein disclosed is an AT gene for complementation group D, the ATDC gene. Fragments of said gene are useful as nucleic acid probes and as polymerase chain reaction (PCR) primers. One embodiment of said ATDC gene comprises the human DNA in cosmids K1 and 4-1 which were deposited at the American Type Culture Collection [ATCC; Rockville, Md. (USA)] on Jun. 16, 1992, respectively under ATCC Nos. 75250 and 75251.

Further disclosed is cDNA from said ATDC gene, preferably a 3 kilobase (kb) cDNA and/or fragments thereof, the entire nucleotide sequence for which is shown in FIGS. 6a-c [SEQ ID NO: 1. Still further disclosed are AT proteins and/or polypeptides translated from said cDNA, preferably from said 3 kb cDNA. The amino acid sequence for a preferred AT protein is shown in FIGS. 7a-d [SEQ ID NO: 3.

Still further disclosed are polymerase chain reaction (PCR) primers for amplifying each of the 9 exons of said 3 kb cDNA. Said primers are delineated in FIG. 9, and the 14 PCR fragments amplified by said primers are shown in FIGS. 10a-n.

Said ATDC gene, fragments thereof and/or the related cDNA are useful as follows: 1) to identify AT proteins and polypeptides as well as homologs or near-homologs thereto, preferably of the AT complementation group D; 2) to identify mutations in ATDC genes leading to AT-D; 3) to identify various mRNAs transcribed from ATDC genes in various AT cell lines and from different human tissues; 4) to provide the means to construct probes to test for persons with AT and that are AT heterozygotes; 5) and to elucidate the mechanisms by which AT mutations lead to radiosensitivity, immunodeficiences and ataxia.

For example, fragments of the ATDC gene as contained in the deposited cosmids K1 and 4-1, or fragments thereof, or the 3 kb cDNA as shown in FIGS. 6a-c and/or fragments thereof, or the PCR primers for each of the nine exons, can be used as probes to identify and isolate ATDC genes from various AT patients. The nucleotide sequences of the ATDC gene from persons with AT and from those without AT can be compared, and the mutation(s) responsible for AT pleiotropic abnormalities can be identified. Once the AT mutation(s) is or are identified, nucleic acid probes, preferably DNA probes, or PCR primers, can be constructed that span the mutated region(s). Such probes or PCR primers will provide the basis for the development of tests, hybridization or PCR assays, to identify people with AT and heterozygote carriers of the mutated AT gene. PCR assays are preferred.

The sequence of the ATDC gene and/or fragments thereof and the resulting probes should allow for research to progress on the mechanism(s) underlying the pleiotropic abnormalities of AT and investigations into the reported high rates of some types of cancers in AT heterozygotes.

Within the scope of this invention are AT proteins and/or polypeptides, preferably ATDC proteins and/or polypeptides, produced recombinantly, chemically and/or biologically, wherein said proteins and/or polypeptides are in a substantially pure form.

BRIEF DESCRIPTION OF THE DRAWINGS

FIG. 1a illustrates the structure of cosmid clones K1 and K41. The locations of the human DNA (thinner black lines) and integrated pCV108 cosmid sequences (unblackened bars) are shown. The neo gene, with an SV40 promoter and bifunctional termination sequences are positioned as shown. The blackened bars indicate restriction fragments in the K1 and K41 cosmids that contain sequences complementary to cDNA from a HeLa cDNA library. The locations of the four EcoRI (E) fragments combined as probes for identification of cDNA clones are shown, as are the locations of the restriction-enzymes sites for BglII (B), SmaI (Sm), SstI (Ss), XbaI (Xb), and XhoI (Xh).

FIG. 1b illustrates the structure of the full-length 3.0 kilobase (kb) cDNA.

FIG. 2a illustrates the structure of the 4-1 and 3-1 cosmids containing the 3' portion of the ATDC gene (the ataxia-telangiectasia complementation group D gene).

FIG. 2b illustrates the structure of the intact ATDC gene, as reconstructed from the sequences in the K1 (left) and 4-1 (right) cosmids. The symbols for the DNA sequences and restriction sites are as defined in the description of FIGS. 1a and b, supra.

FIGS. 6a-c show the nucleotide sequence for the full-length 3 kb cDNA, the restriction map for which is shown in FIG. 1b.

FIGS. 7a-d provide the translated open reading frame nucleotide sequence for the 3 kb cDNA.

FIG. 9 provides the nucleotide sequences for the PCR primers for the 3 kb cDNA, the placement of which is shown schematically in FIG. 8 and specifically in FIGS. 10a-n.

FIGS. 10a-n provide the nucleotide sequences for the PCR fragments of the 3 kb cDNA schematically indicated in FIG. 8 as well as the placement of the PCR primers listed in FIG. 9.

Nucleotide and Amino Acid Sequence Symbols

Figure 3:
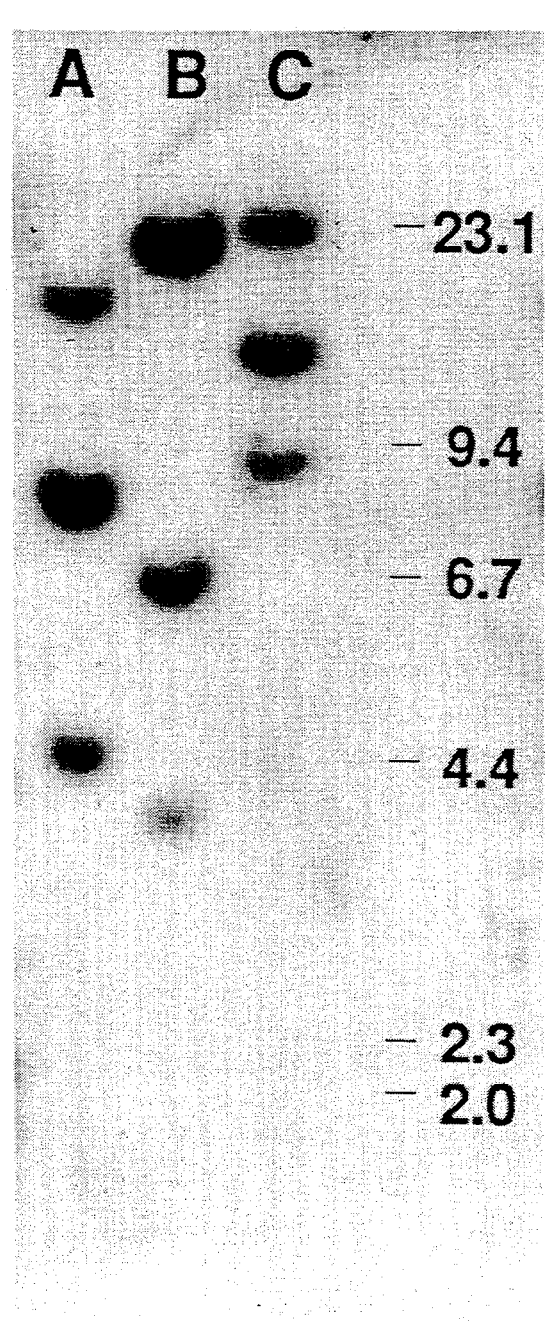
FIG. 3 shows a Southern blot analysis of total human DNA, digested with the restriction enzymes BglII (lane A), EcoRI (lane B), or XbaI (lane C), with the 3.0-kb cDNA as a probe. The positions and sizes (in kilobases) of lambda HindIII restriction fragments are shown.

The following symbols are used to represent nucleotides in the figures herein:

| Base | Symbol |
|---|---|
| adenine | A |
| cytosine | C |
| guanine | G |
| thymine | T |
| uracil | U |

It is understood that because of the degeneracy of the genetic code, that is, that more than one codon will code for one amino acid [for example, the codons TTA, TTG, CTT, CTC, CTA and CTG each code for the amino acid leucine (leu)], that variations of the nucleotide sequence in, for example, FIGS. 6a-c, wherein one codon is substituted for another, would produce a substantially equivalent protein or polypeptide according to this invention. All such variations in the nucleotide sequence of the 3 kb cDNA are included within the scope of this invention.

It is further understood that the nucleotide sequence herein described and shown in FIGS. 6a-c represent only the precise structure of the cDNA nucleotide sequence isolated according to this invention. It is expected that slightly modified nucleotide sequences will be found or can be modified by techniques known in the art to code for substantially similar AT proteins and polypeptides, for example, those having similar epitopes, and such nucleotide sequences and proteins/polypeptides are considered to be equivalents for the purpose of this invention. DNA having equivalent codons is considered within the scope of the invention, as are synthetic DNA sequences that encode proteins/polypeptides homologous or substantially homologous to AT proteins/polypeptides, as well as those sequences but for the degeneracy of the genetic code would hybridize to said 3 kb cDNA nucleotide sequence. Modifications and variations of DNA sequences as indicated herein are considered to result in sequences that are substantially the same as the ATDC sequences and fragments thereof herein.

There are twenty main amino acids, each of which is specified by a different arrangement of three adjacent DNA nucleotides (triplet code or codon), and which are linked together in a specific order to form a characteristic protein. A three-letter convention is used herein to identify said amino acids, as, for example, in FIGS. 7a-d, as follows:

| Amino acid name | Symbol |
|---|---|
| Alanine | Ala |
| Arginine | Arg |
| Asparagine | Asn |
| Aspartic Acid | Asp |
| Cysteine | Cys |
| Glutamic Acid | Glu |
| Glutamine | Gln |
| Glycine | Gly |
| Histidine | His |
| Isoleucine | Ile |
| Leucine | Leu |
| Lysine | Lys |
| Methionine | Met |
| Phenylalanine | Phe |

| Amino acid name | Symbol |
|---|---|
| Proline | Pro |
| Serine | Ser |
| Threonine | Thr |
| Tryptophan | Trp |
| Tyrosine | Tyr |
| Valine | Val |

Abbreviations

The following abbreviations are used herein.
AT—ataxia-telangiectasia
AT-A—ataxia-telangiectasia complementation group A
AT-B—ataxia-telangiectasia complementation group B
AT-C—ataxia-telangiectasia complementation group C
AT-D—ataxia-telangiectasia complementation group D
ATCC—American Type Culture Collection
ATDC gene—AT-D complementing gene
B—BglII
DAPI—diamino-2-phenylindole
E—EcoRI
FITC—fluorescein isothiocyanate
Gy—gray; unit of absorbed radiation according to Systeme International d'Unites
kb—kilobase
M—molar
min—minute
ml—milliliter
PCR—polymerase chain reaction
Sm—SmaI
Ss—SstI
SV—simian virus
μg—micrograms
Xb—XbaI
Xh—XhoI

DETAILED DESCRIPTION

Herein disclosed is a new gene, an AT gene, more specifically the ATDC gene. That gene was isolated by complementation of ionizing radiation sensitivity in an AT cell line from complementation group D. Claimed herein is said ATDC gene and nucleotide sequences that are substantially complementary to said gene or fragments thereof. Strong evidence is provided herein to indicate that a defect in said gene is responsible for radiosensitivity in AT cells of complementation group D.

To isolate that gene, the radiosensitive AT cells of the AT5BIVA cell line were first transfected with a human cosmid library containing a selectable neo gene, followed by selection with both the antibiotic G418 and ionizing radiation to isolate cell clones containing human/cosmid DNA that complements the defective gene. A cell clone (1B3) that demonstrates partial recovery of resistance to ionizing radiation was isolated. That clone was found to contain three integrated human/cosmid sequences.

The integrated human/cosmid sequences were rescued by a process which first comprised the construction of a cosmid library from the 1B3 cell DNA and then the selection with kanamycin for clones containing the neo gene. The selected cosmid clones were then used as chromosome-specific painting probes [Pinkel et al., *PNAS* (USA), 85: 9138–9142 (December 1988); Gray et al., European Patent Application 430,402 (published Jun. 5, 1991); and Ward et al., WO 90/05789 (published May 31, 1990)] for in situ hybridization to chromosomes from normal human lymphocytes. Two related cosmid clones (K1 and K41) were found to contain human sequences that originated from chromosomal region 11q23. As indicated in the Background above, the 11q23 region has been previously determined by genetic linkage analysis to be the location of the AT gene(s) from three separate complementation groups.

Restriction site mapping of the cosmid clones showed that they contain over 36 kilobases (kb) of human DNA located to one side of an integrated cosmid sequence in cell clone 1B3. Southern blot analysis with total human DNA revealed that most of the 36 kb was single-copy DNA. A cDNA library was screened with parts of said single-copy DNA as probes, and two clones that hybridized were isolated, indicating that the ATDC gene is transcribed in relative abundance. Transfection of one of the cosmids (K1) back in the radiosensitive parental AT cell line (AT5BIVA) resulted in the isolation of one cell clone that exhibited radioresistance similar to that for 1B3.

Sequence analysis has shown that ATDC is a previously unidentified gene. Although the ATDC gene is a single-copy gene, five mRNAs have been detected in a range of from about 1.8 kilobases (kb) to about 5.7 kb. The variation in size of the mRNAs may result from differences at the 5' end, indicating that the ATDC gene is a complex gene that can code for several different proteins. The ATDC gene may therefore have multiple functions, consistent with the pleiotropic abnormalities seen in individuals with AT.

Fine mapping of the location of the ATDC gene, as described below, by means of radiation hybrid cell lines, demonstrated that the ATDC gene is located just telomeric to the THY1 marker, that is, in the region that had been indicated by linkage analysis to contain the AT gene from complementation group D.

The ATDC gene and/or fragments thereof and/or cDNA therefrom may be used as probes to identify homologous genes from other AT complementation groups. Linkage analysis has demonstrated that the AT gene(s) for the various complementation groups are clustered together, and thus it is possible that they are distantly related. Chromosome 11-specific libraries, preferably chromosome 11q23-specific libraries, and still more preferably chromosome 11q23-specific cosmid libraries, can be screened to identify clones that cross hybridize with ATDC.

Further, mouse cDNA libraries can be screened with ATDC probes for a related mouse gene. Isolation of a mouse homolog would allow for the development of a transgenic mouse AT model.

The probes and assays enabled by this invention will be useful in proving that a defect in the ATDC gene is responsible for AT-D. Proof required would be (1) the demonstration of genetic rearrangements, such as, deletions, amplifications, translocations, inversions, point mutations among others, in the ATDC gene in AT-D cells, and/or (2) functional complementation of radiosensitivity in AT-D cells after transfection with an appropriate vector, preferably a cosmid vector containing the gene or a fragment thereof, or a cDNA therefrom in an expression vector. That there are no detectable rearrangements within the ATDC gene in the AT5BIVA cell line suggests a small rearrangement or point mutation, as observed in other human genetic diseases [Gibbs et al., *Genomics*, 7: 235–244 (1990); Groden et al., *Cell*, 66: 589–600 (1991)]. DNA from other AT cell lines from unknown complementation groups also showed no identifiable alterations in the ATDC gene. Preferably sequence analysis of the ATDC gene in cells obtained exclusively from AT-D individuals will be used to determine whether mutations in the gene are associated with AT.

Assays to Detect Mutations in the ATDC Gene

An important utility of the instant invention is to detect the mutations that cause defect(s) in the ATDC gene resulting in the phenotypic symptoms of AT-D. To detect relatively large genetic rearrangments, hybridization tests, preferably Southern or Northern assays, can be used. To detect relatively small genetic rearrangements, as for example, small deletions or amplifications, or point mutations, assays incorporating PCR are preferably used.

Preferred methods of identifying mutations within the ATDC gene comprise assays wherein PCR is used. The mechanics of PCR are described in Saiki et al., *Science*, 230: 1350 (1985) and U.S. Pat. Nos. 4,800,159 (issued Jan. 24, 1989), 4,683,195 and 4,683,202 (both of the latter issued Jul. 28, 1987). Preferably, such a PCR assay amplifies and analyses cellular DNA, such that mutations within splice sites as well as within coding regions can be detected when appropriate primers are used. However, mRNA could also be isolated, and cDNA prepared therefrom. Appropriate PCR primers could then be used to amplify the cDNA, and the cDNA PCR products from normal and AT cells could then be compared.

An exemplary PCR assay is that wherein the PCR primers listed in FIG. 9 are used. In such an assay, cellular DNA from people with AT and without AT is isolated and amplified with the PCR primers. The PCR products from the normal and AT cells are compared, preferably initially upon a sizing gel. Changes in size indicative of certain genetic rearrangements are thus determined. If no changes are found in the size of the fragments, then further comparisons can be made to detect genetic rearrangements that would not be evident in such a size comparison, for example, deletions of a few base pairs or point mutations. To effect such further comparisons, preferred methods include the use of a PCR-single-strand conformation polymorphism (PCR-SSCP) assay or a denaturing gradient gel electrophoretic assay. The PCR-SSCP method is described in a review article by Kenshi Hayashi entitled "PCR-SSCP: A Simple and Sensitive Method for Detection of Mutations in the Genomic DNA" in *PCR Methods and Applications*, 1: 34–38 (1991). Denaturing gradient gel electrophoresis is described in Myers et al., "Detection and Localization of Single Base Changes by Denaturing Gradient Gel Electrophoresis," *Methods in Enzymology*, 155: 501–527 (1987).

Such assays, as hybridization and PCR assays, preferably PCR assays including the PCR-SSCP or denaturing gradient gel electrophoretic assays, as applied in the context of this invention may be used to screen people for AT heterozygosity, which can be a significant risk factor in regard, for example, to ionizing radiation, and for prenatal testing for and diagnosis of AT, among other uses.

AT Proteins and/or Polypeptides

The phrase "AT proteins and/or polypeptides" is herein defined to mean proteins and/or polypeptides encoded by an ATDC gene and/or fragments thereof. An exemplary and preferred AT protein is that for which the amino acid sequence is shown in FIGS. 7a–d [SEQ ID NO: 3].

A "polypeptide" is a chain of amino acids covalently bound by peptide linkages and is herein considered to be composed of 50 or less amino acids. A "protein" is herein defined to be a polypeptide composed of more than 50 amino acids.

It will be appreciated that the amino acid sequence of AT proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention.

The AT proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare AT proteins is by recombinant means.

A representative method to prepare the AT protein as shown in FIGS. 7a–d or fragments thereof would be to insert the appropriate fragment of the 3 kb cDNA pictured in FIGS. 6a–c into an appropriate expression vector. A wide variety of host-cloning vector combinations may be usefully employed in cloning the ATDC DNA isolated as described herein. For example, useful cloning vehicles may include chromosomal, nonchromosomal and synthetic DNA sequences such as various known bacterial plasmids such as pBR322, other E. coli plasmids and their derivatives and wider host range plasmids such as RP4, phage DNA such as the numerous derivatives of phage lambda, e.g., NB989 and vectors derived from combinations of plasmids and phage DNAs such as plasmids which have been modified to employ phage DNA expression control sequences.

Useful hosts may be eukaryotic or prokaryotic and include bacterial hosts such as E. coli and other bacterial strains, yeasts and other fungi, animal or plant hosts such as animal or plant cells in culture, insect cells and other hosts. Of course, not all hosts may be equally efficient. The particular selection of host-cloning vehicle combination may be made by those of skill in the art after due consideration of the principles set forth herein without departing from the scope of this invention.

The particular site chosen for insertion of the selected DNA fragment into the cloning vehicle to form a recombinant DNA molecule is determined by a variety of factors. These include size and structure of the protein or polypeptide to be expressed, susceptibility of the desired protein or polypeptide to endoenzymatic degradation by the host cell components and contamination by its proteins, expression characteristics such as the location of start and stop codons, and other factors recognized by those of skill in the art.

The recombinant nucleic acid molecule containing the ATDC gene, fragment thereof, or cDNA thereform, may be employed to transform a host so as to permit that host (transformant) to express the structural gene or fragment thereof and to produce the protein or polypeptide for which the hybrid DNA codes. The recombinant nucleic acid molecule may also be employed to transform a host so as to permit that host on replication to produce additional recombinant nucleic acid molecules as a source of ATDC DNA and fragments thereof. The selection of an appropriate host for either of these uses is controlled by a number of factors recognized in the art. These include, for example, compatibility with the chosen vector, toxicity of the co-products, ease of recovery of the desired protein or polypeptide, expression characteristics, biosafety and costs.

Where the host cell is a procaryote such as E. coli, competent cells which are capable of DNA uptake are prepared from cells harvested after exponential growth phase and subsequently treated by the $CaCl_2$ method by well known procedures. Transformation can also be performed after forming a protoplast of the host cell.

Where the host used is an eucaryote, transfection method of DNA as calcium phosphate-precipitate, conventional mechanical procedures such as microinjection, insertion of a plasmid encapsulated in red blood cell hosts or in liposomes, treatment of cells with agents such as lysophosphatidyl-choline or use of virus vectors, or the like may be used.

The level of production of protein or polypeptide is governed by two major factors: the number of copies of its gene or DNA sequence encoding for it within the cell and the efficiency with which these gene and sequence copies are transcribed and translated. Efficiencies of transcription and translation (which together comprise expression) are in turn dependent upon nucleotide sequences, normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to known expression control sequences so as to favor higher levels of expression. This having been achieved, the newly engineered DNA fragment may be inserted into a multicopy plasmid or a bacteriophage derivative in order to increase the number of gene or sequence copies within the cell and thereby further improve the yield of expressed protein.

Several expression control sequences may be employed. These include the operator, promoter and ribosome binding and interaction sequences (including sequences such as the Shine-Dalgarno sequences) of the lactose operon of E. coli ("the lac system"), the corresponding sequences of the tryptophan synthetase system of E. coli ("the trp system"), a fusion of the trp and lac promoter ("the tac system"), the major operator and promoter regions of phage lambda ($O_L P_L$ and $O_R P_R$), and the control region of the phage fd coat protein. DNA fragments containing these sequences are excised by cleavage with restriction enzymes from the DNA isolated from transducing phages that carry the lac or trp operons, or from the DNA of phage lambda or fd. These fragments are then manipulated in order to obtain a limited population of molecules such that the essential controlling sequences can be joined very close to, or in juxtaposition with, the initiation codon of the coding sequence.

The fusion product is then inserted into a cloning vehicle for transformation of the appropriate hosts and the level of antigen production is measured. Cells giving the most efficient expression may be thus selected. Alternatively, cloning vechicles carrying the lac, trp or lambda $P_L$ control system attached to an initiation codon may be employed and fused to a fragment containing a sequence coding for an AT protein or polypeptide such that the gene or sequence is correctly translated from the initiation codon of the cloning vehicle.

The phrase "recombinant nucleic acid molecule" is herein defined to mean a hybrid nucleotide sequence comprising at least two nucleotide sequences, the first sequence not normally being found together in nature with the second.

The phrase "expression control sequence" is herein defined to mean a DNA sequence of nucleotides that controls and regulates expression of structural genes when operatively linked to those genes.

Synthetic and Biologic Production of AT Proteins and Polypeptides

AT proteins and polypeptides of this invention may be prepared not only by recombinant means but also by synthetic and by other biologic means. Exemplary of other biologic means to prepare the desired polypeptide or protein is to subject to selective proteolysis a longer AT polypeptide or protein containing the desired amino acid sequence; for example, the longer polypeptide or protein can be split with chemical reagents or with enzymes. Synthetic formation of the polypeptide or protein requires chemically synthesizing the desired chain of amino acids by methods well known in the art.

Chemical synthesis of a peptide is conventional in the art and can be accomplished, for example, by the Merrifield solid phase synthesis technique [Merrifield, J., *Am. Chem. Soc.*, 85: 2149–2154 (1963); Kent et al., *Synthetic Peptides in Biology and Medicine*, 29 f.f. eds. Alitalo et al., (Elsevier Science Publishers 1985); and Haug, *ABL*, 40–47 (January/February 1987)].

Techniques of chemical peptide synthesis include using automatic peptide synthesizers employing commercially available protected amino acids, for example, Biosearch [San Rafael, Calif. (USA)] Models 9500 and 9600; Applied Biosystems, Inc. [Foster City, Calif. (USA)] Model 430; Milligen [a division of Millipore Corp.; Bedford, Mass. (USA)] Model 9050; and Du Pont's RAMP (Rapid Automated Multiple Peptide Synthesis) [Du Pont Compass, Wilmington, Del. (USA)].

The following materials and methods were used in the examples illustrating this invention.

Cell Lines

The simian virus (SV)40-transformed cell lines LM217 (normal) and AT2SF (unknown AT complementation group) were established by transfection of primary human fibroblasts with pSVori- plasmid [Murnane et al., *Exp. Cell Res.*, 158: 119–126 (1985); Murnane et al., *Mol. Cell Biol.*, 6: 549–558 (1986)].

The SV40-transformed fibroblast cell line AT3BISV (AT-A) was provided by A. M. R. Taylor (Birmingham, United Kingdom).

Cell line 1B3 was derived from the SV40transformed fibroblast cell line AT5BIVA (GM5849) [Kapp and Painter 1989, supra], which was obtained from the NIGMS Human Genetic Mutant Cell Repository [Camden, N.J. (USA)]. HeLa cells (Hela S3; ATCC CCL 2.2) were obtained from the American Type Culture Collection [ATCC; Rockville, Md. (USA)].

Cosmid Library Construction

The cosmid library from 1B3 was constructed according to standard procedures [Sambrook et al., "Molecular Cloning: A Laboratory Manual" 2d ed (Cold Spring Harbor Laboratory, Cold Spring Harbor, N.Y.; 1989)]. DNA from 1B3 was partially digested with MboI, and fragments of about 30 kilobases (kb) to about 50 kb were ligated to BamHI-digested pWE16 cosmid DNA [Stratagene, La Jolla, Calif. (USA); Wahl et al., PNAS, 84: 2160 (1987)]. Clones containing the neo (neomycin resistance) gene in the integrated pCV108 cosmid [Lau and Kan, PNAS, 80: 5225 (1983)] DNA originally used for transfection [Kapp and Painter (1989)] were selected by growth of the XL1-Blue bacteria (Stratagene) containing the cosmid library on agar plates with 50 μg kanamycin/ml. Restriction-enzyme mapping was accomplished by digestion with various combinations of enzymes and was confirmed by further mapping of the individual EcoRI fragments cloned into a Bluescript plasmid (Stratagene).

Cosmid and cDNA Library Screening

A commercially available HeLa cell cDNA library (Stratagene) within the bacteriophage vector ZAPII was screened according to a method described elsewhere [Murnane, *Mol. Cell Biol.*, 6: 549–558 (1986)] with a probe that consisted of cosmid fragments containing only nonrepetitive sequences. Positive cDNA clones were then rescued from ZAPII by in vivo excision of the Bluescript plasmid by using a protocol provided with the vector (Stratagene). A chromosome 11-specific cosmid library obtained from L. Deaven [Los Alamos National Laboratory; Los Alamos, N. Mex. (USA)] was screened by conventional methods (Sambrook et al. 1989, supra) with the use of a 3.0 kb cDNA as a probe (FIGS. 1b, 6a–c, and 10a–n).

Southern and RNA Blot Analysis

Preparation of high-molecular-weight cellular DNA and Southern blot analysis were as described elsewhere (Murnane 1986, supra). mRNA was prepared with the use of an mRNA isolation kit [Fast Track®; Invitrogen; San Diego, Calif. (USA)]. RNA agarose gel electrophoresis and RNA blot analysis were carried out according to standard procedures (Sambrook et al. 1989, supra).

Functional Complementation

DNA to be tested for complementation was introduced into AT5BIVA cells by calcium phosphate-mediated transfection (Murnane et al. 1985, supra). Before transfection, the cosmid clones were linearized with NotI, which cuts between the vector and human sequences. Cell clones containing the integrated DNA were selected by incubation with 400 μg G418/ml. X-ray survival was determined according to a method described elsewhere (Kapp and Painter 1989, supra) with or without feeder layers that consisted of HeLa cells exposed to 60 Gy (gray) of X-rays.

In Situ Hybridization

Metaphase spreads were prepared according to the method described by Yunis in *Science*, 191: 1268–1270 (1976). Slides were treated with 20 μg pepsin/ml (in 0.1M HCl) for 10 min at 37° C. before in situ hybridization. Hybridization conditions and staining procedures were modified from those of Pinkel et al. [*PNAS* (USA), 83: 2934–2938 (1986)] and Trask et al. [*Am. J. Hum. Genet.*, 48: 1–15 (1991)]. The in situ hybridization probe strategy specifically comprised the use of a dioxigenin-labeled K1 or K2 cosmid probe that was detected with FITC-conjugated antibodies, and a biotin-labeled chromosome 11-specific alpha-satellite DNA probe that was detected with Texas Red-conjugated avidin. The chromosome 11-specific alpha-satellite DNA probe was used as a marker in locating the origin of the cosmid probes to human chromosomal region 11q23 Chromosomes were counterstained with 4',6-diamino-2-phenylindole (DAPI).

Radiation Hybrid Mapping

The chromosomal map location of the ATDC gene was determined by a radiation hybrid mapping technique [Richard et al., *Am. J. Hum. Genet.*, 49: 1189–1196 (1991)]. The order and distances between ATDC and the markers stromelysin 1 (STMY1), CJ52.193 (D11S384), CJ52.77 (D11S424), CD3D, apolipoprotein (APO), THY1, D11S528, or ETS1 were established by a statistical analysis of the cosegregation of markers in 100 radiation hybrids, and the method of moments was used to determine the frequency of breakage between markers [Cox et al., *Science*, 250: 245–250 (1990)]. Because a single retention frequency was used in this analysis, and since each hybrid was scored for almost every marker, the likelihood for any marker order was estimated as the sum of the pairwise lod scores between markers. The map with the highest likelihood was defined as that map in which the sum of lod scores between adjacent loci was maximized. The polymerase chain reaction (PCR) with primers specific for the 3' end of the 3.0 kb cDNA (primers 9D-5 and 9D-3 shown in FIG. 9) was used to determine which of the radiation hybrids contained the ATDC gene. The conditions for PCR were the same as those used for mapping other markers on human chromosome 11q (Richard et al. 1991, supra).

The following examples are for purposes of illustration only and are not meant to limit the invention in any way.

EXAMPLE 1

Isolation of Integrated Cosmid DNA

The integrated cosmid sequences from cell line 1B3 were isolated by construction of a cosmid library from 1B3 DNA, and then by using kanamycin to select bacteria that had cosmids containing the integrated neo gene. Cosmid clones isolated by this method were screened by in situ hybridization to identify cosmids containing human DNA from the chromosomal region 11q23, previously demonstrated to be the location of the gene(s) associated with three AT complementation groups. Two of the cosmid clones (K1 and K41) hybridized to chromosomal region 11q23. As indicated above, a dioxigenin-labeled K1 or K2 cosmid probe was localized to 11q23 in a chromosome-specific painting experiment wherein a chromosome 11-specific alpha-satellite DNA probe was used concurrently to identify the centromeric chromosome 11 region.

The rescue from the integration site in 1B3 of DNA that originated from the chromosomal region 11q23 is further strong evidence that a gene within the transfected DNA complements radiosensitivity in cells from AT-D. According to restriction-enzyme mapping, K1 and K41 contained overlapping sequences, consisting of both the integrated pCV108 cosmid and adjacent human DNA (FIG. 1a).

To determine whether the cloned human DNA contained any expressed cellular genes, fragments of cosmid K1 were used as probes to screen a HeLa cell cDNA library. Four adjacent EcoRI fragments that contained only nonrepetitive cellular DNA (FIG. 1a) were combined for this purpose. After hybridization to $1.2 \times 10^6$ cDNA clones, 40 positive plaques were identified. Restriction-enzyme mapping of nine of these cDNA clones demonstrated that they were all related and that the five largest (3.0 kb) were nearly identicial (FIG. 1b). Partial sequence analysis of the ends of the 3.0-kb cDNAs has identified the 3' end by the presence of a tract of poly-A and suggests that they are full length because the 5' ends show two stop codons before the first methionine codon in the only complete open reading frame. [Full nucleotide sequence of 3 kb cDNA is shown in FIGS. 6a–c.] That gene contained within those cosmids is herein termed the "AT-D complementing (ATDC) gene."

The approximate position of the sequences complementary to the cDNA within the K1 cosmid was determined by Southern blot analysis. Southern blots of K1 cosmid DNA digested with various restriction enzymes were hybridized with either the full-length 3.0-kb cDNA or a fragment from the 5' end. By the location of the labeled restriction fragments, two separate regions of hybridization were identified (FIG. 1a). Hybridization with the fragment from the 5' end of the cDNA indicated that the direction of transcription in the cosmid was from left to right (FIG. 1a). Consistent with those results are the similarity of the restriction sites (XhoI, SstI, and SmaI) between the cDNA and cosmid clones (FIG. 1), as well as partial sequence analysis, which also demonstrated that the region of hybridization to the left (FIG. 1a) coded for the 5' end of the transcript.

Not all of the sequences found in the cDNA were contained within the K1 and K41 cosmids. This was evident from the absence of additional hybridization regions containing SstI and EcoRI restriction sites corresponding to those found within the cDNA and indicates that nearly half of the coding sequences within the cDNA were absent from these cosmids. The fact that the transfected pCV108 sequences were located adjacent to the ATDC gene in both the K1 and K41 cosmid clones shows that the truncated gene is the form integrated into cell line 1B3. The orientation of the integrated sequences placed the SV40 bidirectional transcriptional termination sequences, which are located adjacent to the neo gene in the pCV108 cosmid, downstream from the truncated gene (FIG. 1a). The form of the ATDC gene integrated into cell line 1B3 is therefore a functional transcriptional unit despite the absence of the 3' end.

The presence of only a portion of the ATDC gene in 1B3 can explain several properties of 1B3, namely: (a) radiosensitivity in 1B3 did not completely return to the level seen in normal cells [Kapp and Painter 1989, supra]; (b) 1B3 amplified the integrated DNA, whereas other independently derived, related clones that did not amplify the integrated cosmid sequences failed to maintain radioresistance in culture [Kapp and Painter 1989]; and (c) 1B3 cells continued to show radioresistant DNA synthesis similar to that of the parental AT5BIVA cell line [Kapp and Painter 1989].

EXAMPLE 2

Isolation of the 3' End of the ATDC Gene and Composite Mapping of the ATDC Gene To obtain the missing portion of the ATDC gene, the cDNA was used as a probe to screen a human genomic chromosome 11 library. Two cosmid clones (3-1 and 4-1) were identified. Restriction mapping of these clones demonstrated that they contained overlapping regions (FIG. 2a). With the use of the 3.0-kb cDNA (FIGS. 1b and 6a-c) as a probe, Southern blot analysis revealed three separate regions of hybridization within the cosmid DNA (FIG. 2a). One of these regions, which was contained within cosmid clone 4-1 but not within 3-1, overlapped with cosmid clones K1 and K41 (FIG. 2a). That was determined by sequence analysis with primers derived from the cDNA sequence. Beyond the overlapping region (compare FIGS. 1a and 2a), the differences between K1 and 4-1 are apparently due to the rearrangements that occurred in K1 during transfection and that resulted in the loss of the 3' end of the gene. Cosmid clone 4-1 therefore contains the ATDC gene 3' portion that was missing from clones K1 and K41. A composite map derived from cosmid clones K1 and 4-1 indicates that the missing 3' portion of the ATDC gene is more than 30 kb in length (FIG. 2b).

Southern blot analysis of human genomic DNA from normal cells with the 3.0-kb cDNA as a probe (FIG. 3) was consistent with the structure of the gene predicted from restriction-enzyme mapping analysis of the cosmid clones (FIG. 2b). Bands detected after digestion of human DNA with BglII (1.8, 4.5, 8.0, and 15 kb), EcoRI (4.0, 6.0, and 20 kb), and XbaI (9.0, 12, and 23 kb) all corresponded to the expected fragments. The 1.8-kb BglII fragment contains only a small number of complementary sequences and is difficult to detect. The absence of additional bands demonstrates that no other genes complementary to the ATDC gene are present in the human genome. Southern blot analysis of DNA isolated from the parental SV40-transformed AT fibroblast cell line, AT5BIVA, as well as two other SV40-transformed AT fibroblast cell lines (AT3BISV, AT-A; AT2SF, unknown complementation group) gave results identical to those from the normal cell DNA.

EXAMPLE 3

Characterization of mRNA Transcripts

Figure 4:
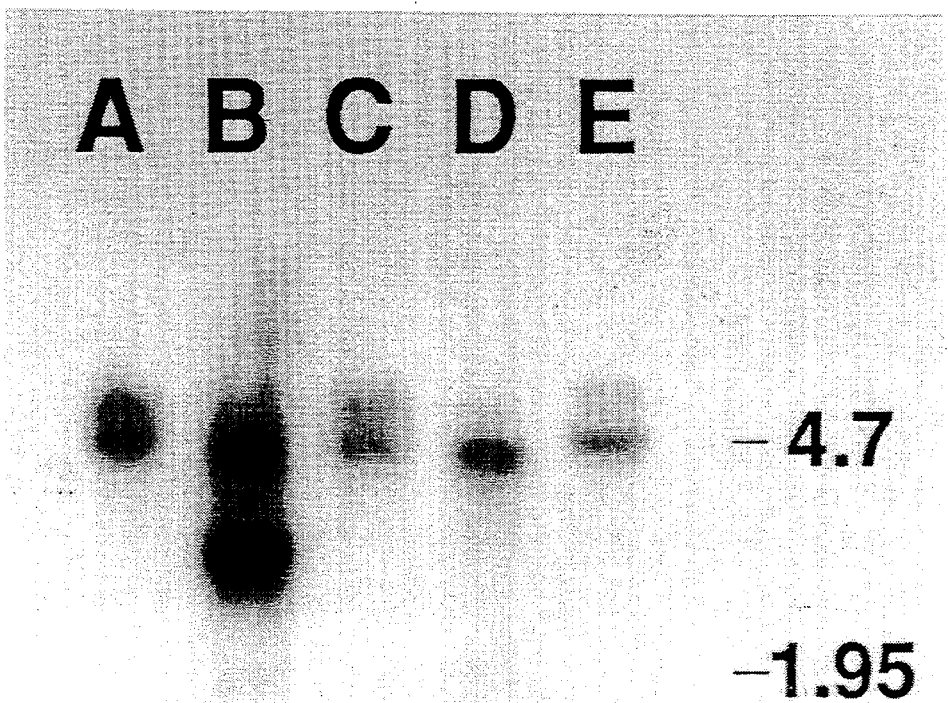
FIG. 4 shows a RNA blot analysis of poly-A-selected mRNA from cell lines LM217 (lane A), HeLa (lane B), 1B3 (lane C), AT3BISV (lane D), and AT5BIVA (lane E), with the 3.0-kb cDNA as a probe. The positions of human and bacterial ribosomal RNA size markers (in kilobases) are shown.

Although ATDC is a single-copy gene, it produces several mRNAs of varous sizes (FIG. 4), apparently because of alternate processing of RNA transcripts. RNA blot analysis of mRNA isolated from an SV40-transformed fibroblast cell line (LM217) demonstrated two mRNA transcripts (5.7 and 4.7 kb) that hybridized to the cDNA probe. In contrast, mRNA isolated from HeLa cells lacked the largest mRNA transcript (seen more clearly on shorter exposures), and instead contained at least two others (3.0 and 1.8 kb). In HeLa cells, the 3.0-kb mRNA transcript was the most abundant, consistent with the fact that the cDNA for this mRNA was the only one identified in the HeLa cell library (FIG. 1b).

Two SV40-transformed AT fibroblast cell lines (AT3BISV and AT5BIVA) contained various amounts of the mRNA transcripts seen in the LM217 and HeLa cells. In contrast, the 1B3 cell line appeared identical to the SV40-transformed normal line LM217, in size of mRNAs. The significance of the differences between the mRNA observed in the AT3BISV and AT5BIVA cell lines and that seen in LM217 or 1B3 is not known. No additional mRNA transcript from the truncated ATDC gene was evident in 1B3, indicating that it is either below the level of detection or is similar in size to one of the mRNAs transcribed from the endogenous gene.

The production of multiple mRNAs has been observed with other mammalian genes and can result from multiple promoters, alternate splicing, and/or alternate poly-A addition sites [Leff et al., Ann. Rev. Biochem., 55: 1091-1117 (1986)]. The presence of different mRNAs in epithelial (HeLa) and fibroblast (LM217, 1B3, AT5-BIVA, and AT3BISV) cell lines (FIG. 4) could indicate tissue-specific processing of ATDC mRNA [Leff et al., 1986, id.] which would be consistent with the pleiotropic characteristics of AT. Because the 3.0-kb mRNA that produced the cDNA that was isolated from HeLa cells is not found in the LM217 cell line, functional complementation of radioresistance may require the cDNA from the 4.7-kb mRNA, which is present in both HeLa and LM217.

EXAMPLE 4

Functional Complementation

After transfection of AT5BIVA cells with the K1 cosmid, 50 G418-resistant clones were tested for sensitivity to X-rays. Three clones showed increased radioresistance; one of them (C6) had about the same radioresistance as did the 1B3 cell line (FIG. 5).

Figure 5:
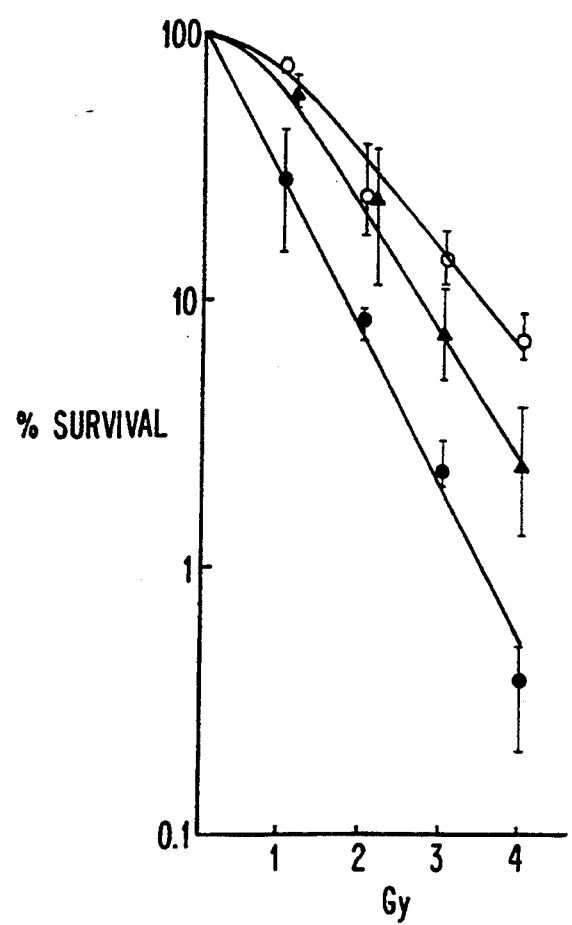
FIG. 5 provides a graph of survival as a function of X-ray dose for the following cell lines: AT5BIVA (indicated by blackened circle); 1B3 (indicated by unblackened circles); and C6 (indicated by blackened triangles).
Figure 8:
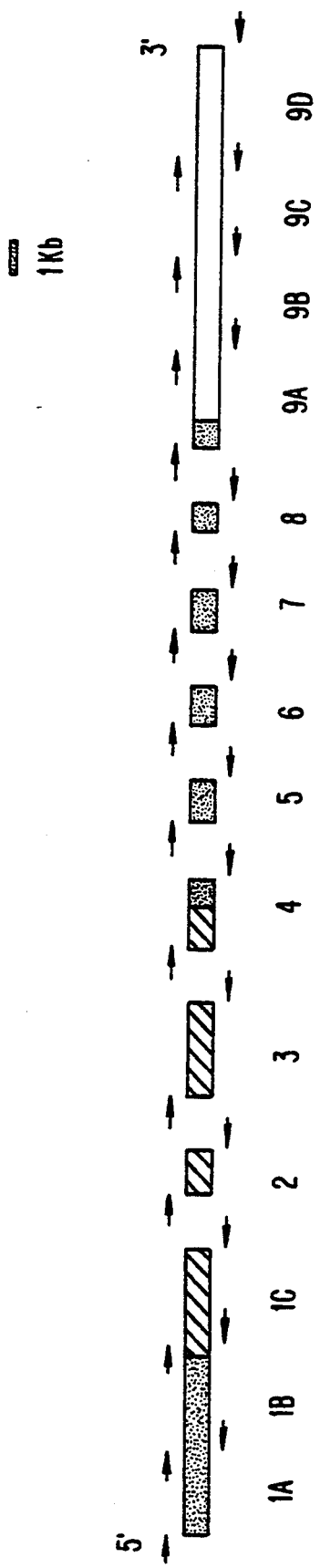
FIG. 8 schematically shows the nine exons of the 3 kb cDNA. Fourteen PCR fragments are delineated wherein the arrows indicate the positions of the primers. The primers are shown in FIG. 9, and the sequences of the PCR fragments in FIGS. 10a-n. The open box indicates the untranslated region whereas the hatched boxes indicate the region of the alpha helix.

Thus, these initial functional complementation studies achieved a partial restoration of radioresistance in the AT5BIVA cell line as shown in FIG. 5. The absence of full complementation with the K1 cosmid could be due to several factors. The large size of the ATDC gene may make complementation difficult because of the problems associated with integrating large intact DNA fragments into human cells [Colbere-Garapin et al., Gene, 50: 279-288 (1986); Hoeijmakers et al., Exp. Cell Res., 169: 111-119 (1987); Mayne et al., Gene, 66: 65-76 (1988) (erratum: Gene, 83: 395 (1989)]. Furthermore, because the ATDC gene produces mRNAs larger than the 3.0-kb mRNA characterized herein, it is unclear whether the K1 cosmid contains all of the coding sequences transfected into 1B3.

EXAMPLE 5

Fine Mapping of the Chromosomal Location of the ATDC Gene

Radiation hybrids that contained mapped fragments of human chromosome 11 (Richard et al. 1991, supra) were used to determine the location of the ATDC gene. The position of the ATDC gene relative to known markers within 11q23 was established by using PCR to identify which of the radiation hybrids contained the gene. Statistical analysis of 100 radiation hybrid cell lines showed that the ATDC gene is closely linked to THY1 and D11S528, with lod scores of 12.2 and 17, respectively (Table 1). The order 11cen-APO-CD3D-

THY1-ATDC-11qtel was 1,000 times more likely than the order 11cen-APO-CD3D-ATDC-THY11-11qtel which places the ATDC gene centromeric to THY1.

Thus, the ATDC gene lies outside the linkage region predicted to contain the AT gene(s) for complementation groups A and C, indicating a separate locus for the complementation group D gene. The results described herein clearly demonstrate that the ATDC gene is not linked to the centromeric (STMY1) and telomeric (D11S424) flanking markers for the AT-A and AT-C gene(s). However, the evidence that the ATDC gene isolated from 1B3 is telomeric to THY1 is consistent with the evidence for an additional AT gene within that region. It appears from the evidence that several genes within the 11q23 region are associated with AT; the lack of hybridization of ATDC to other human DNA sequences suggests that they are not closely related.

TABLE 1

Radiation Hybrid Two-Point Mapping Analysis of ATDC and Various Chromosome 11 Loci

| Marker | | | | No. of Clones Observed[c] | | | | |
|---|---|---|---|---|---|---|---|---|
| A | B | $cR_{9000}{}^{a}$ | $LOD^b$ | ++ | +− | −+ | −− | Total |
| ATDC | STMY1 | | .5 | 7 | 13 | 15 | 64 | 99 |
| ATDC | D11S384 | | 1.4 | 9 | 11 | 14 | 65 | 99 |
| ATDC | D11S424 | | 1.0 | 8 | 12 | 13 | 66 | 99 |
| ATDC | APO | 81 | 3.1 | 10 | 10 | 8 | 71 | 99 |
| ATDC | CD3D | 37 | 7.7 | 13 | 7 | 3 | 76 | 99 |
| ATDC | THY1 | 17 | 12.2 | 15 | 5 | 0 | 79 | 99 |
| ATDC | D11S528 | 6 | 17.0 | 18 | 2 | 0 | 79 | 99 |
| ATDC | ETS1 | | 2.0 | 9 | 11 | 10 | 69 | 99 |
| APO | CD3D | 28 | 9.5 | 14 | 5 | 3 | 78 | 100 |
| APO | THY1 | 50 | 5.3 | 11 | 8 | 5 | 76 | 100 |
| CD3D | THY1 | 17 | 11.7 | 14 | 3 | 2 | 81 | 100 |

[a]Represents distances (in centiRays), which are shown only for linked markers (LOD > 3).
[b]Likelihood that two markers are linked.
[c]Number of hybrids that retain both markers A and B (++), marker A but not marker B (+−), marker B but not marker A (−+), or neither marker A nor B (−−); total number of hybrids analyzed is also shown.

The materials listed below were deposited with the American Type Culture Collection (ATCC) in Rockville, Md. (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The organism will be made available by the ATCC under the terms of the Budapest Treaty, and subject to an agreement between the Applicants and the ATCC which assures unrestricted availability upon issuance of the pertinent U.S. Patent. Availability of the deposited strain is not to be construed as a license to practice the invention in contravention of the rights granted under the authority of any Government in accordance with its patent laws.

| Cosmid | Deposit Date | ATCC # |
|---|---|---|
| K1 | June 16, 1992 | >75250 |
| 4-1 | June 16, 1992 | >75251 |

The description of the foregoing embodiments of the invention have been presented for purposes of illustration and description. They are not intented to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated. It is intended that the scope of the invention be defined by the claims appended hereto.

All references cited herein are hereby incorporated by reference.

We claim:

1. An isolated nucleic acid selected from the group consisting of: SEQ ID NO: 1, SEQ ID NO: 2, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 42, SEQ ID NO: 43, SEQ ID NO: 44, and SEQ ID NO: 45; the human Ataxia Telangiectasia Complementation Group D (ATDC) nucleotide sequences in cosmids K1 and 4-1, which were deposited at the American Type Culture Collection (ATCC), respectively under ATCC Nos. 75250 and 75251.

2. The isolated nucleic acid according to claim 1 which is SEQ. ID. NO.: 1.

3. The isolated nucleic acid sequence according to claim 1 which is SEQ. ID. NO.: 2.

4. The isolated nucleic acid sequence according to claim 1 which is selected from the group consisting of the human ATDC nucleotide sequences contained in cosmids K1 and 4-1.

5. The isolated nucleic acid according to claim 1 selected from the group consisting of SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 40, SEQ ID NO: 42, SEQ ID NO: 43, SEQ ID NO: 44, SEQ ID NO: 45.

6. An isolated nucleic acid having a sequence encoding the amino acid sequence of SEQ. ID. NO.: 3.

7. A vector comprising an expression control sequence operatively linked to the isolated nucleic acid according to claim 6.

8. An isolated nucleic acid, useful as a nucleic acid probe to identify Ataxia-Telangiectasia Complementation Group D (ATDC) nucleotide sequences, selected from the group consisting of restriction fragments of the human ATDC nucleotide sequences contained in cosmids K1 and 4-1, which were deposited at the American Type Culture Collection (ATCC), respectively under ATCC Nos. 75250 and 75251, wherein the restriction enzymes used to generate said fragments are selected from the group consisting of EcoRI, BglII, SmaI, SstI, XbaI and XhoI.

9. The isolated nucleic acid according to claim 8 which is an EcoRI restriction fragment.

10. A composition comprising cosmid K1 or cosmid 4-1 which were deposited at the American Type Culture Collection (ATCC), respectively under ATCC Nos. 75250 and 75251, and a carrier.

* * * * *